US012354493B2

(12) United States Patent
Stanko et al.

(10) Patent No.: US 12,354,493 B2
(45) Date of Patent: Jul. 8, 2025

(54) OPTIC ULTRASOUND TRAINING SIMULATOR

(71) Applicant: The University of Toledo, Toledo, OH (US)

(72) Inventors: Kelley Stanko, Toledo, OH (US); Yixing Chen, Toledo, OH (US); Daniel Brainard, Toledo, OH (US)

(73) Assignee: The University of Toledo, Toledo, OH (US)

( * ) Notice: Subject to any disclaimer, the term of this patent is extended or adjusted under 35 U.S.C. 154(b) by 1799 days.

(21) Appl. No.: 16/385,589

(22) Filed: Apr. 16, 2019

(65) Prior Publication Data

US 2019/0325786 A1  Oct. 24, 2019

Related U.S. Application Data

(60) Provisional application No. 62/659,927, filed on Apr. 19, 2018.

(51) Int. Cl.
| | |
|---|---|
| *G09B 23/28* | (2006.01) |
| *A61B 8/10* | (2006.01) |
| *A61F 2/14* | (2006.01) |
| *B29C 64/106* | (2017.01) |
| *B29D 11/02* | (2006.01) |
| *G06T 7/60* | (2017.01) |

(52) U.S. Cl.
CPC .............. *G09B 23/286* (2013.01); *A61B 8/10* (2013.01); *B29C 64/106* (2017.08); *B29D 11/02* (2013.01); *G06T 7/60* (2013.01); *A61F 2/14* (2013.01)

(58) Field of Classification Search
USPC ....................................................... 434/271
See application file for complete search history.

(56) References Cited

U.S. PATENT DOCUMENTS

| | | | | |
|---|---|---|---|---|
| 2,688,139 | A | * | 9/1954 | Jardon ..................... A61F 2/141 433/201.1 |
| 4,865,551 | A | * | 9/1989 | Maloney ................ G09B 23/30 623/5.11 |
| 4,865,552 | A | * | 9/1989 | Maloney ................ G09B 23/30 434/271 |
| 5,893,719 | A | * | 4/1999 | Radow ................... G09B 23/28 434/271 |

(Continued)

FOREIGN PATENT DOCUMENTS

| | | | | | |
|---|---|---|---|---|---|
| KR | 20170011752 | A | * | 2/2017 | ............. G09B 23/28 |
| WO | WO-2016089395 | A1 | * | 6/2016 | ............... A61B 3/00 |
| WO | WO-2018097031 | A1 | * | 5/2018 | ........... A61F 9/0017 |

OTHER PUBLICATIONS

Xie et al., "Application of 3-Dimensional Printing Technology to Construct an Eye Model for Fundus Viewing Study" PLOS ONE | www.plosone.org Nov. 1, 2014 | vol. 9 | Issue 11 | e109373 (Year: 2014).*

(Continued)

*Primary Examiner* — Xuan M Thai
*Assistant Examiner* — Andrew Bodendorf
(74) *Attorney, Agent, or Firm* — MacMillan, Sobanski & Todd, LLC

(57) ABSTRACT

Ocular ultrasound models, and ocular ultrasound training simulators using the same, along with methods of making and using the same, are described.

24 Claims, 34 Drawing Sheets

(56) References Cited

U.S. PATENT DOCUMENTS

| | | | | |
|---|---|---|---|---|
| 6,569,373 | B2* | 5/2003 | Napadensky | B41M 3/006 264/494 |
| 6,887,083 | B2* | 5/2005 | Umeyama | G09B 23/30 434/271 |
| 8,128,412 | B2* | 3/2012 | Carda | G09B 23/30 434/271 |
| 8,137,111 | B2* | 3/2012 | Carda | G09B 23/30 434/271 |
| 8,845,334 | B1* | 9/2014 | Stoll | G09B 23/28 434/270 |
| 9,437,119 | B1* | 9/2016 | Bernal | G09B 23/34 |
| 10,290,236 | B2* | 5/2019 | Bernal | G09B 23/34 |
| 11,394,901 | B2* | 7/2022 | Riedel | A61B 3/0025 |
| 2002/0028429 | A1* | 3/2002 | Umeyama | G09B 23/30 434/271 |
| 2004/0126746 | A1* | 7/2004 | Toly | G09B 23/28 434/262 |
| 2008/0099636 | A1* | 5/2008 | Depay | G06F 1/1605 248/74.2 |
| 2009/0004636 | A1* | 1/2009 | Carda | G09B 23/30 434/271 |
| 2009/0004637 | A1* | 1/2009 | Carda | G09B 23/30 434/271 |
| 2011/0067624 | A1* | 3/2011 | Cain | G09B 23/286 116/203 |
| 2011/0181836 | A1* | 7/2011 | Rowe | G09B 23/34 351/205 |
| 2012/0021397 | A1* | 1/2012 | Van Dalen | G09B 23/30 434/271 |
| 2012/0193582 | A1* | 8/2012 | Boutet | G09B 23/286 264/28 |
| 2013/0030524 | A1* | 1/2013 | Akura | G09B 23/34 264/2.7 |
| 2015/0037775 | A1* | 2/2015 | Ottensmeyer | G09B 23/286 434/262 |
| 2015/0131053 | A1* | 5/2015 | Copland | A61B 3/1005 351/246 |
| 2015/0279239 | A1* | 10/2015 | Chang | G09B 23/30 434/271 |
| 2016/0063898 | A1* | 3/2016 | Bernal | G09B 23/306 434/271 |
| 2016/0098944 | A1* | 4/2016 | Lin | G09B 23/32 434/271 |
| 2016/0372011 | A1* | 12/2016 | Bernal | G09B 23/34 |
| 2017/0014169 | A1* | 1/2017 | Dean | A61B 17/8071 |
| 2018/0350269 | A1* | 12/2018 | Gada | G09B 9/00 |
| 2019/0122584 | A1* | 4/2019 | McAlpine | C09D 11/30 |
| 2019/0213917 | A1* | 7/2019 | Yates | G09B 23/30 |
| 2019/0244543 | A1* | 8/2019 | Turk | G09B 23/30 |
| 2019/0318661 | A1* | 10/2019 | Bernal | G16H 50/50 |
| 2019/0362654 | A1* | 11/2019 | Omata | G09B 23/285 |
| 2021/0248927 | A1* | 8/2021 | Segall | G09B 23/32 |

OTHER PUBLICATIONS

Blaivas et al., "Elevated Intracranial Pressure Detected by Bedside Emergency Ultrasonography of the Optic Nerve Sheath", Acadmeic Emergency Medicine, 2003, vol. 10, No. 4, pp. 376-381.

"8th WinFocus World Congress on Ultrasound in Emergency and Critical Care", Critical Ultrasound Journal, 2012, vol. 4, Suppl. 1, pp. 1-13.

Jafri et al., "An Inexpensive and Easy Simulation Model of Ocular Ultrasound That Mimics Normal Anatomy as Well as Abnormal Ophthalmologic Conditions", American Institute of Ultrasound in Medicine, 2011, vol. 30, pp. 569-573.

Murphy et al., "Validation of a Low-cost Optic Nerve Sheath Ultrasound Phantom: An Educational Tool", Journal of Medical Ultrasound, 2017, vol. 25, pp. 96-100.

Teismann et al., "Point-of-care Ocular Ultrasound to Detect Optic Disc Swelling", Academic Emergency Medicine, 2013, vol. 20, No. 9, pp. 920-925.

Trace et al., "Radiology's Emerging Role in 3-D Printing Applications in Health Care", Journal of the American College of Radiology, 2016, vol. 13, No. 7, pp. 856-862.e4.

Yoonessi, et al., "Bedside Ocular Ultrasound for the Detection of Retinal Detachment in the Emergency Department", Society for Academic Emergency Medicine, 2010, vol. 17, No. 9, pp. 913-917.

* cited by examiner

OPTIC ULTRASOUND TRAINING SIMULATOR

RELATED APPLICATIONS

This application claims priority to U.S. Provisional Application No. 62/659,927, filed under 35 U.S.C. § 111(b) on Apr. 19, 2018, the disclosure of which is incorporated herein by reference in its entirety.

STATEMENT REGARDING FEDERALLY SPONSORED RESEARCH

This invention was made with no government support. The government has no rights in this invention.

BACKGROUND

Ultrasound operates on the principle that sound waves travel at different speeds when they encounter tissues of different densities. Ultrasound waves are reflected back to the transducer by tissue in its path. When the sound wave returns, it causes vibration of the crystal in the transducer and results in electrical impules that are translated into an image on the screen. Because the eye is a superficial fluid-filled structure of largely consistent density, ultrasound is an easy-to-use modality for visualization of ocular pathology and anatomy.

The use of ocular ultrasound on emergency patients has recently been adopted by emergency physicians to evaluate for ocular pathology and emergencies. Direct visualization of ocular structures is difficult or impossible when the eye lids are swollen shut after injury. Lens opacification and hyphema can also block the view into the posterior chamber. Point of care ultrasound (POCUS) has been found to be highly accurate diagnosing and evaluating for ocular pathology in patients presenting in emergency departments. However, ultrasound training models are rare and not widely utilized for ocular ultrasound.

Historically, if learners wanted to learn or practice ocular ultrasound, they have been restricted to using live models, which often do not have pathology, learning on the fly in the department on actual patients, and looking at pictures online and in textbooks, which is not necessarily the most effective way to learn POCUS. Hands-on learning, or "probe time" as it can be known, is ultimately the most effective technique for learners to acquire the skill and comfort level needed to use POCUS for clinical decision making There is thus a need in the art for an ocular ultrasound training platform.

SUMMARY

Provided is an ocular ultrasound model comprising a globe having an anterior section and a posterior section, either of (i) a first inner wall and a second inner wall or (ii) a rod extending from the globe at the posterior section, a first side wall extending at a first angle from a line tangent to a middle point on a first side of the globe, a second side wall extending at a second angle from a line tangent to a middle point on a second side of the globe, and a bottom wall extending between the two side walls, wherein the first and second inner walls or the rod extend from the globe to the bottom wall.

In certain embodiments, the ocular ultrasound model further comprises an enclosed chamber disposed within the anterior section. In particular embodiments, the enclosed chamber is formed from a first arc and a second arc, wherein the first arc is concave and the second arc is convex, the first arc having a different length than the second arc.

In certain embodiments, the first and second angles are each from about 0° to about 20°. In particular embodiments, the first and second angles are each from about 5° to about 10°. In certain embodiments, the first angle approximately equals the second angle.

In certain embodiments, the first and second inner walls are substantially parallel to each other.

In certain embodiments, the ocular ultrasound model comprises acrylonitrile butadiene styrene (ABS) or polylactic acid (PLA). In certain embodiments, the globe, the first and second inner walls or the rod, the first and second side walls, and the bottom wall all comprise the same plastic material.

In certain embodiments, the ocular ultrasound model further comprises a gelatinous substance in the globe.

In certain embodiments, the ocular ultrasound model comprises a first ultrasoundable chamber between the first side wall and the first inner wall, and a second ultrasoundable chamber between the second side wall and the second inner wall.

Further provided is an ocular ultrasound model comprising a globe having an anterior section and a posterior section, wherein the globe has an inner surface and an outer surface, either first and second inner walls or a rod extending from the globe at the posterior section, a first arc within the globe extending between two points on the inner surface, wherein the first arc comprises an anterior surface and a posterior surface, and a second arc within the globe extending between two points on the anterior surface of the first arc, wherein the first arc and the second arc define two chambers within the anterior section of the globe.

In certain embodiments, one of the first arc or the second arc is concentric with the globe. In certain embodiments, the ocular ultrasound model comprises acrylonitrile butadiene styrene (ABS) or polylactic acid (PLA). In certain embodiments, the ocular ultrasound model is filled with a gelatinous substance.

Further provided is an ocular ultrasound model comprising a globe having an anterior section and a posterior section, and first and second inner walls extending from the globe at the posterior section, wherein the globe and the two inner walls comprise the same plastic material, and wherein the ocular ultrasound model provides a representation of a human eye upon exposure to ultrasound waves. In certain embodiments, the ocular ultrasound model comprises acrylonitrile butadiene styrene (ABS) or polylactic acid (PLA). In certain embodiments, the ocular ultrasound model is filled with a gelatinous substance.

Further provided is an ocular ultrasound model comprising a substantially spherical globe comprising an enclosed chamber which provides a representation, upon application of ultrasound waves, of a lens of a human eye, and walls or a rod extending from the globe which provide a representation, upon application of ultrasound waves, of an optic nerve of a human eye, wherein the entire ocular ultrasound model comprises the a plastic material. In certain embodiments, the plastic material comprises acrylonitrile butadiene styrene (ABS) or polylactic acid (PLA). In certain embodiments, the ocular ultrasound model provides a representation of an abnormal pathology. In certain embodiments, the ocular ultrasound model is filled with a gelatinous substance.

Further provided is an ocular ultrasound model as described herein having a retinal wall extending from a first point on an inner surface of the globe to a space within the globe near a second point on the inner surface, where the retinal wall does not cross more than half a width of the globe, the ocular ultrasound model providing a representation under ultrasound of a human eye having a retinal detachment.

Further provided is an ocular ultrasound model as described herein where the inner walls define an optic nerve chamber between the globe and the bottom wall, and where the optic nerve chamber has a narrower section and a wider section, the ocular ultrasound model providing a representation under ultrasound of a human eye having increased optic nerve size. In certain embodiments, the narrower section has a diameter of about 3 mm, and the wider section has a diameter of about 7-8 mm.

Further provided is an ocular ultrasound model as described herein further comprising a foreign body wall extending from an inner surface of the globe, the ocular ultrasound model providing a representation under ultrasound of a human eye having an intraocular foreign body.

Further provided is an ocular ultrasound model as described herein further comprising a speckled area within the globe defined by a curvy wall extending between two points on an inner surface of the globe, wherein the curvy wall crosses over more than half a width of the globe, the ocular ultrasound model providing a representation under ultrasound of a human eye having a vitreous hemorrhage.

Further provided is an ocular ultrasound model as described herein further comprising a speckled area defined by a curvy wall extending from a first point on an inner surface of the globe to a space near, but not touching, a second point on the inner surface, wherein the curvy wall crosses over more than half a width of the globe, the ocular ultrasound model providing a representation under ultrasound of a human eye having a vitreous detachment.

Further provided is an ocular ultrasound model as described herein further comprising a dislocated lens chamber formed in a posterior section of the globe, the ocular ultrasound model providing a representation under ultrasound of a human eye having a dislocated lens.

Further provided is an ocular ultrasound model as described herein further comprising a curvy wall extending from a first point on an inner surface of the globe to a second point on the inner surface of the globe, wherein the curvy wall defines a reduced globe space between the first arc and the curvy wall having a volume less than the volume of a space between the curvy wall and the globe in the posterior section, the ocular ultrasound model providing a representation under ultrasound of a human eye having a ruptured globe.

Further provided is an ocular ultrasound model as described herein further comprising a foreign body wall extending from an inner surface of the globe, and a speckled area within the globe defined by a curvy wall extending between two points on an inner surface of the globe, wherein the curvy wall crosses over more than half a width of the globe, the ocular ultrasound model providing a representation under ultrasound of a human eye having an intraocular foreign body and a vitreous hemorrhage.

Further provided is an ultrasoundable 3D-printed model of a human eye.

Further provided is an ocular ultrasound training simulator comprising a representation of a human head having two sockets designed to receive ocular ultrasound models, and an ocular ultrasound model as described herein in at least one of the sockets. In certain embodiments, the two sockets comprise different ocular ultrasound models.

Further provided is a kit comprising a first container housing a representation of a human head having two sockets configured to receive ocular ultrasound models, and a second container housing at least one ocular ultrasound model. In certain embodiments, the ocular ultrasound models are 3D-printed. In certain embodiments, the kit includes ocular ultrasound models of each of a normal eye, retinal detachment, lens dislocation, vitreous hemorrhage, foreign body, globe rupture, and increased optic nerve diameter.

Further provided is a method of 3D-printing an ocular ultrasound model, the method comprising 3D printing a model out of a single plastic material with a layer height ranging from about 0.10 mm to about 0.25 mm, a shell of about 0.5 mm, a fill of about 100%, a speed of about 35 mm/s, a nozzle temperature of about 240° C., and a bed temperature of about 125° C. In certain embodiments, the plastic material comprises acrylonitrile butadiene styrene (ABS) or polylactic acid (PLA).

BRIEF DESCRIPTION OF THE DRAWINGS

FIG. 4B includes an imaginary midline and two imaginary tangent lines, for the purpose of illustration.

FIGS. 14A-14B show an ocular ultrasound training simulator that is a representation of a whole human head, whereas FIGS. 14C-14D show an ocular ultrasound training simulator that is a representation of a human head only from the middle of the forehead to the bottom of the nose. FIG. 14E shows a photograph of an alternative embodiment of an ocular ultrasound training simulator.

DETAILED DESCRIPTION

Figure 1A:
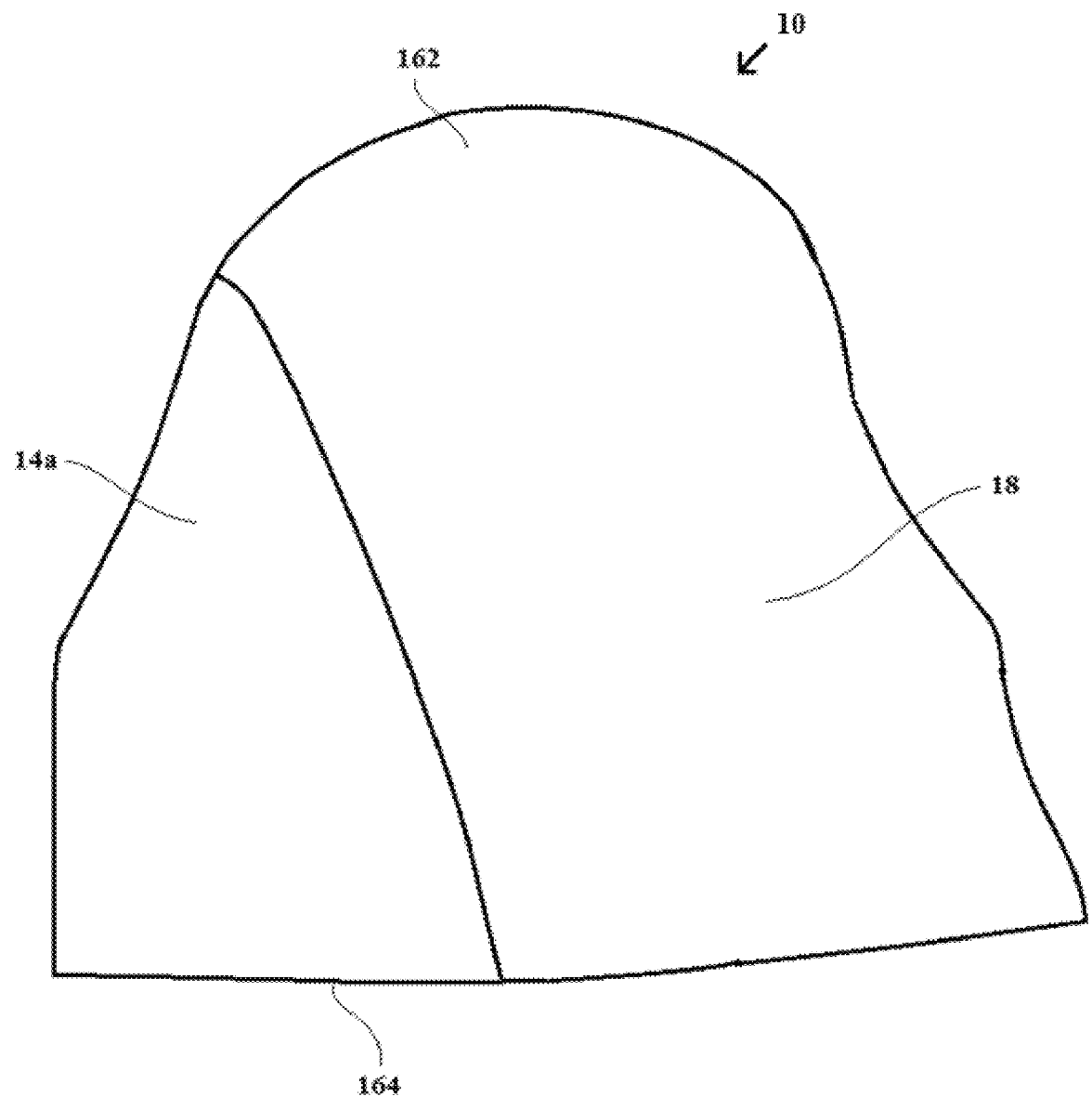
FIGS. 1A-1B: Illustration (FIG. 1A) and photograph (FIG. 1B) of an ocular ultrasound model. Visible in FIG. 1B is a rough surface of the model where the printing substrate was peeled off following 3D printing.

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

Provided herein are 3D printed models of the eye that allow for an anatomically faithful representation of anatomy and pathology when used with ultrasound, along with methods of making and using the same, including as parts of a kit.

3D printing involves the use of different types of materials (generally plastics, though there are biological materials that may be 3D printed) that are heated to melting and then extruded through a nozzle onto a platform. Before anything is printed, 3D animators use computer programs to build computer models of what is to be printed. There are numerous variables and settings involved beyond just the design and shape of the object to be printed, such as the type of material used, the temperature of the extruder, the shape and size of the nozzle, the speed of the printing, and so on.

Thus far, there has been little to no research in the ultrasound simulation art, in the healthcare field, on the uses and utilities of 3D printed models. Indeed, there is a significant technical hurdle that must be overcome in order to successfully 3D print ultrasound models which fairly represent anatomy. This is because air easily gets trapped in the walls of 3D printed models given how the material is extruded into layers. As those skilled in the art know, air is the enemy of ultrasound. Ultrasound waves reflect strongly wherever air meets biological tissue or other material. So, even a small bubble of air will reflect ultrasound waves away instead of allowing them to penetrate the material being examined Surprisingly, in accordance with the present disclosure, this challenge has been overcome by adjusting printing variables in the 3D printing process.

As the examples herein show, utlrasoundable ocular models were initially attempted to be 3D printed using PLA with default printing settings. However, it was found that these printed parts did not produce a good enough ultrasound image to represent the human eye. Without wishing to be bound by theory, it is believed this was due to air being trapped in the layers of the PLA material from the printing process. In order to overcome the problem of air being trapped in the layers of material, various parameters such as the size, temperature, and material were changed. ABS was printed at a higher temperature, which fixed most of the air problems that had been observed. Furthermore, various changes were made to the design of the models in order to eliminate unwanted reflections, as further described in the examples herein.

Provided herein is a normal eye model that creates anatomically accurate images under ultrasound that are comparable to live tissue. Also provided are eye models which create anatomically accurate images of ocular pathology which POCUS lends itself to most readily. As non-limiting examples, retinal detachment, lens dislocation, vitreous hemorrhage, foreign body, globe rupture, and increased optic nerve diameter can be represented through the use of ocular ultrasound models as described herein. The normal and abnormal models can be used for training purposes, for instance to train emergency medical personnel in diagnosing eye pathologies.

Figure 1B:
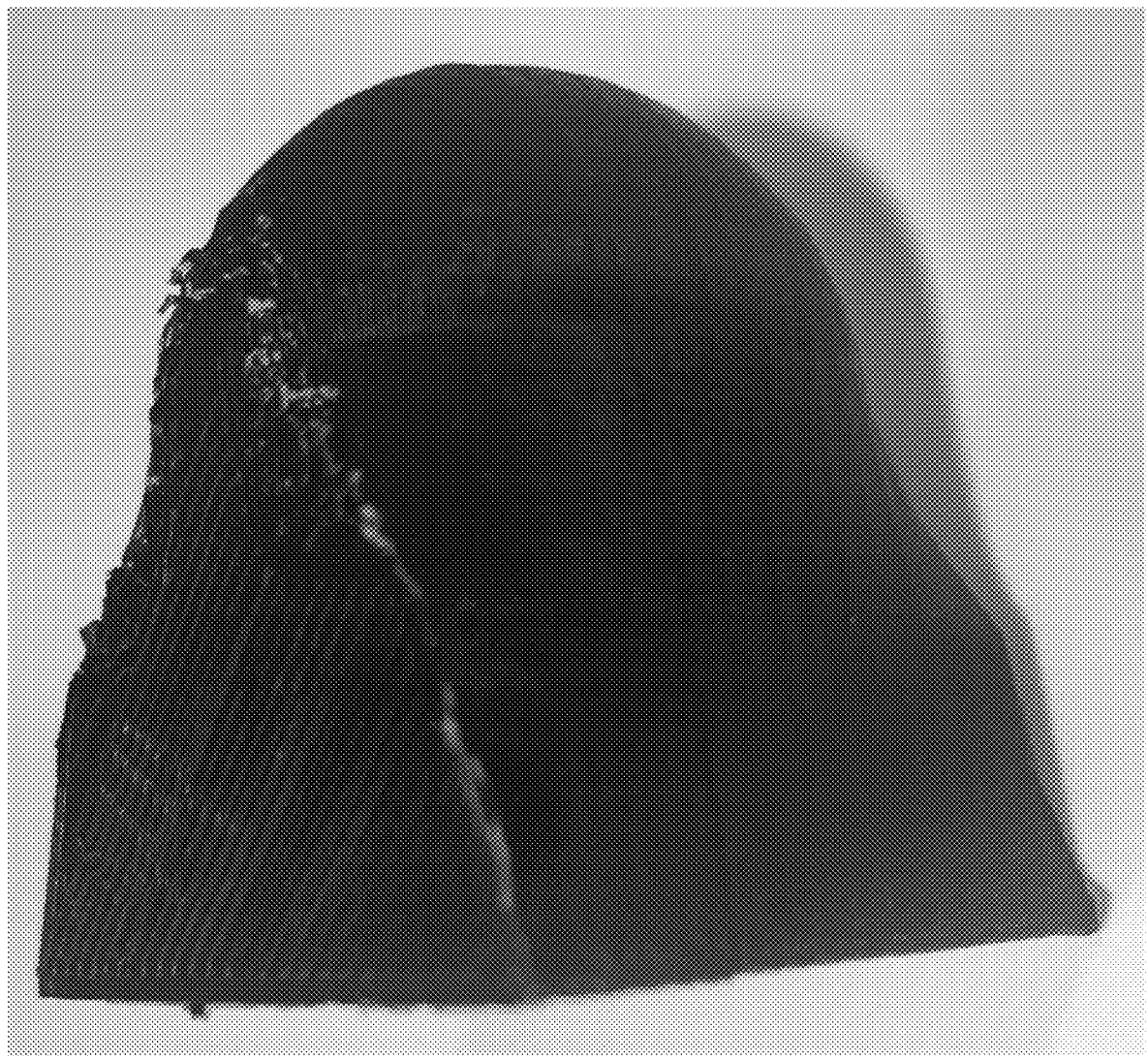
Figure 2:
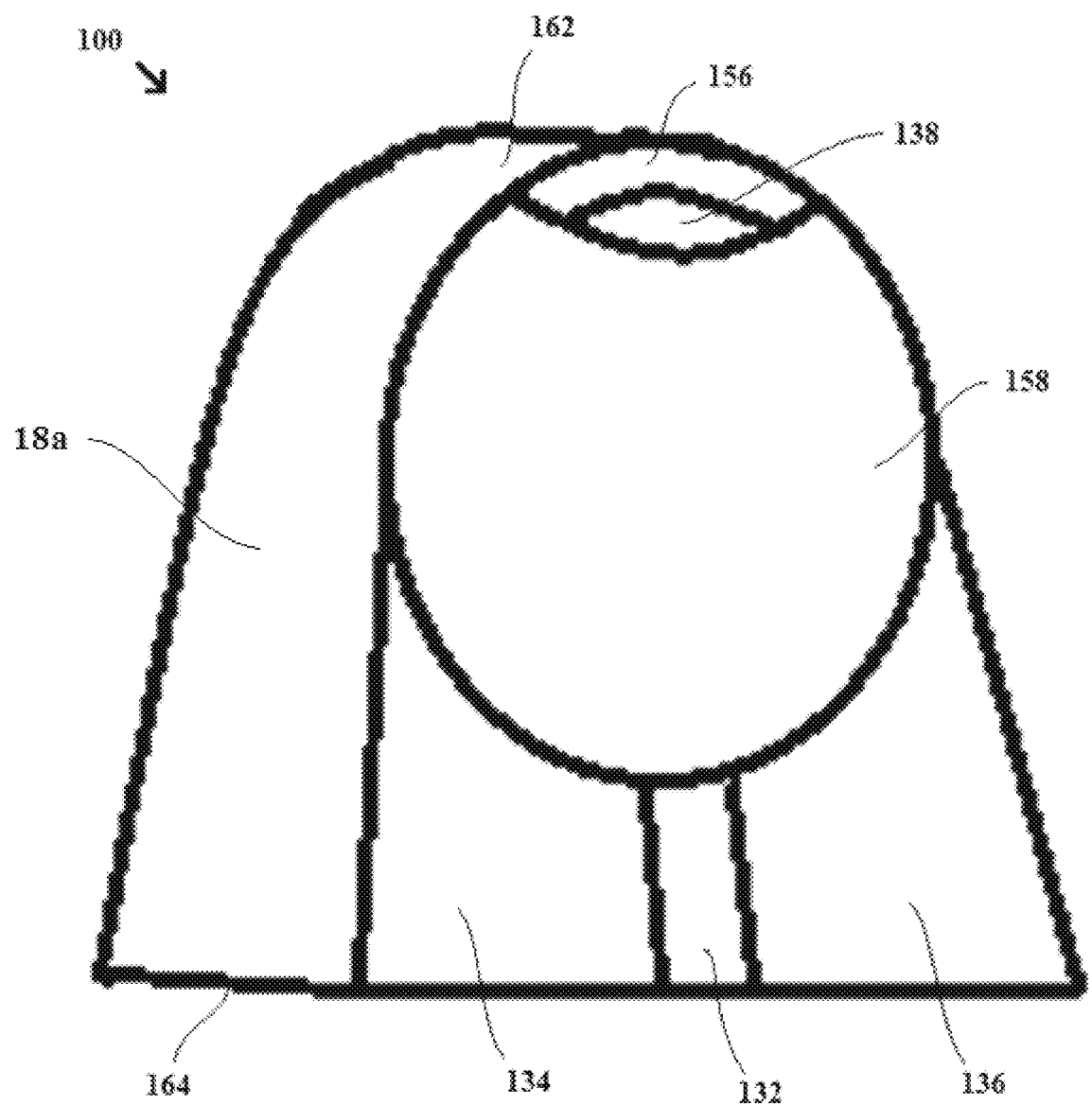
FIG. 2: Perspective view of an ocular ultrasound model segment.
Figure 3A:
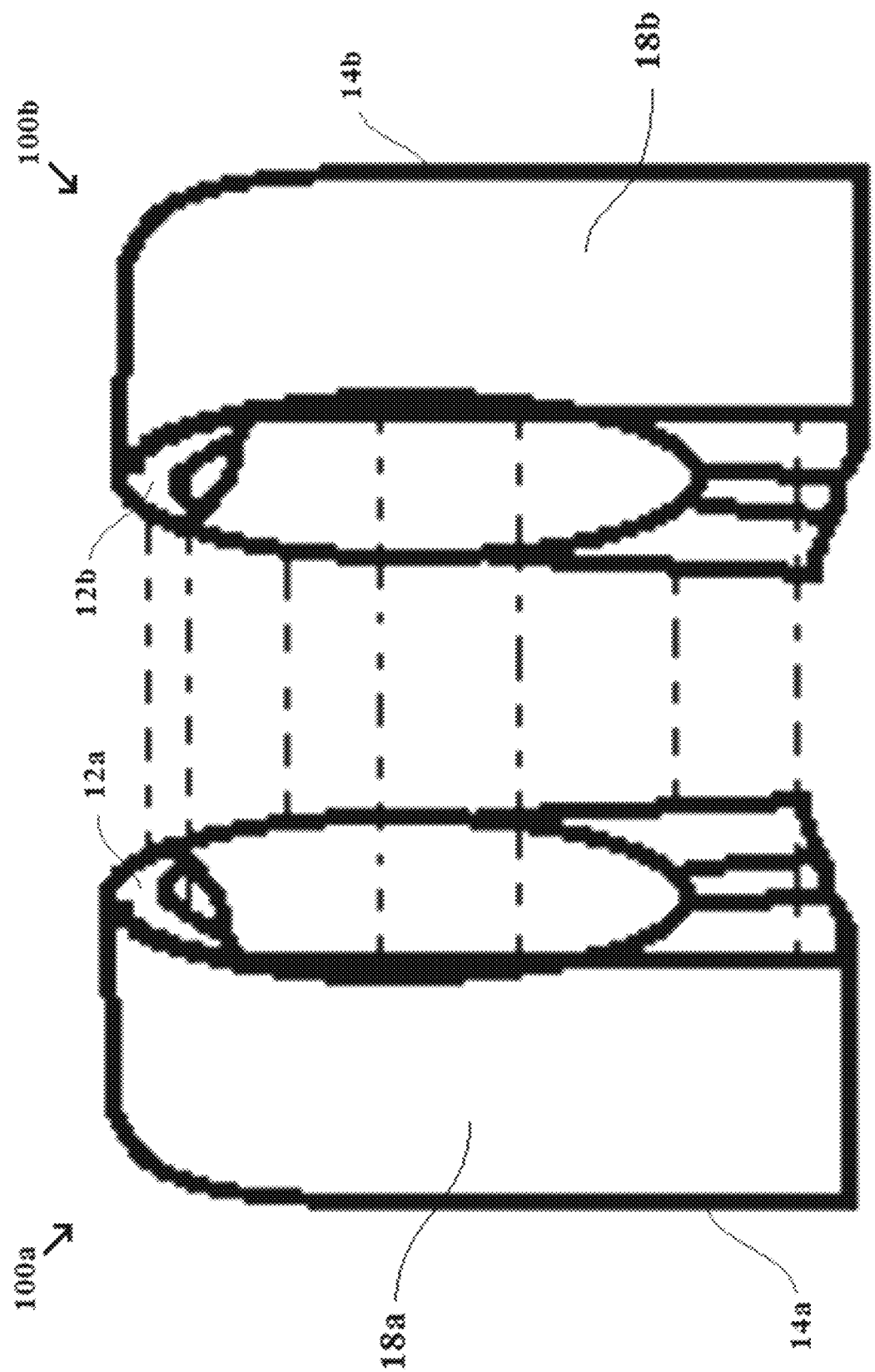
FIGS. 3A-3B: Perspective view (FIG. 3A) and photograph (FIG. 3B) of two segments of an ocular ultrasound model prior to being sealed together. The dotted lines connect surfaces on the two segments that are joined when the segments are sealed together.
Figure 3B:
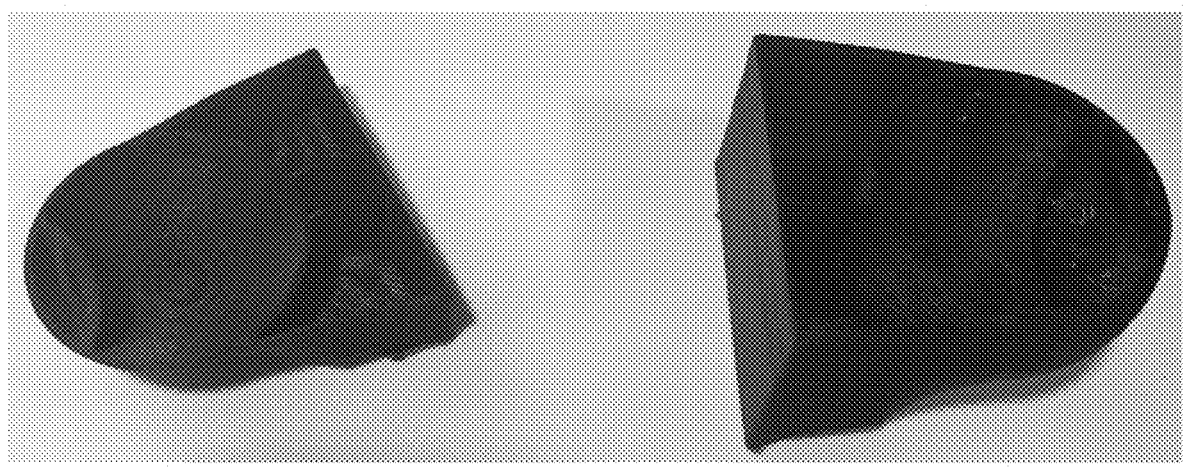

The ocular ultrasound models described herein can be 3D printed in two segments which are sealed together after filling the ocular ultrasound model with a suitable gel substance, described in more detail below. FIGS. 1A-1B show an ocular ultrasound model 10 as assembled. As examples, the two segments can be printed as two equal-sized half segments or, alternatively, as different-sized segments such as a one-third segment and a two-thirds segment. FIG. 3A depicts two equal-sized segments 100a, 100b which may be adhered together to form an ocular ultrasound model 10. FIG. 3B shows a photograph of two 3D-printed unequal-sized segments lying on a surface. FIG. 2 is a perspective view of a segment 100. FIG. 3A shows segments 100a, 100b and uses dotted lines to illustrate the joining of the segments 100a, 100b when pressed together to assemble the ocular ultrasound model 10.

As shown in FIG. 3A, the two segments 100a, 100b each have a front face 12a, 12b and a rear face 14a, 14b, where the front faces 12a, 12b are pressed together to assemble the ocular ultrasound model 10. Respective sides of the segments 100a, 100b come together to form a single side of the assembled ocular ultrasound model 10. For example, the first side 18a, 18b of the segments 100a, 100b join together to form a first side 18 of the assembled ocular ultrasound model 10. The segments 100a, 100b are filled with a suitable gelatinous substance prior to being sealed together, and are then sealed with a suitable adhesive such as super glue. Any gelatinous substance may be used so long as the resulting ocular ultrasound model 10 provides a fair representation of a human eye on an ultrasound image.

Figure 4A:
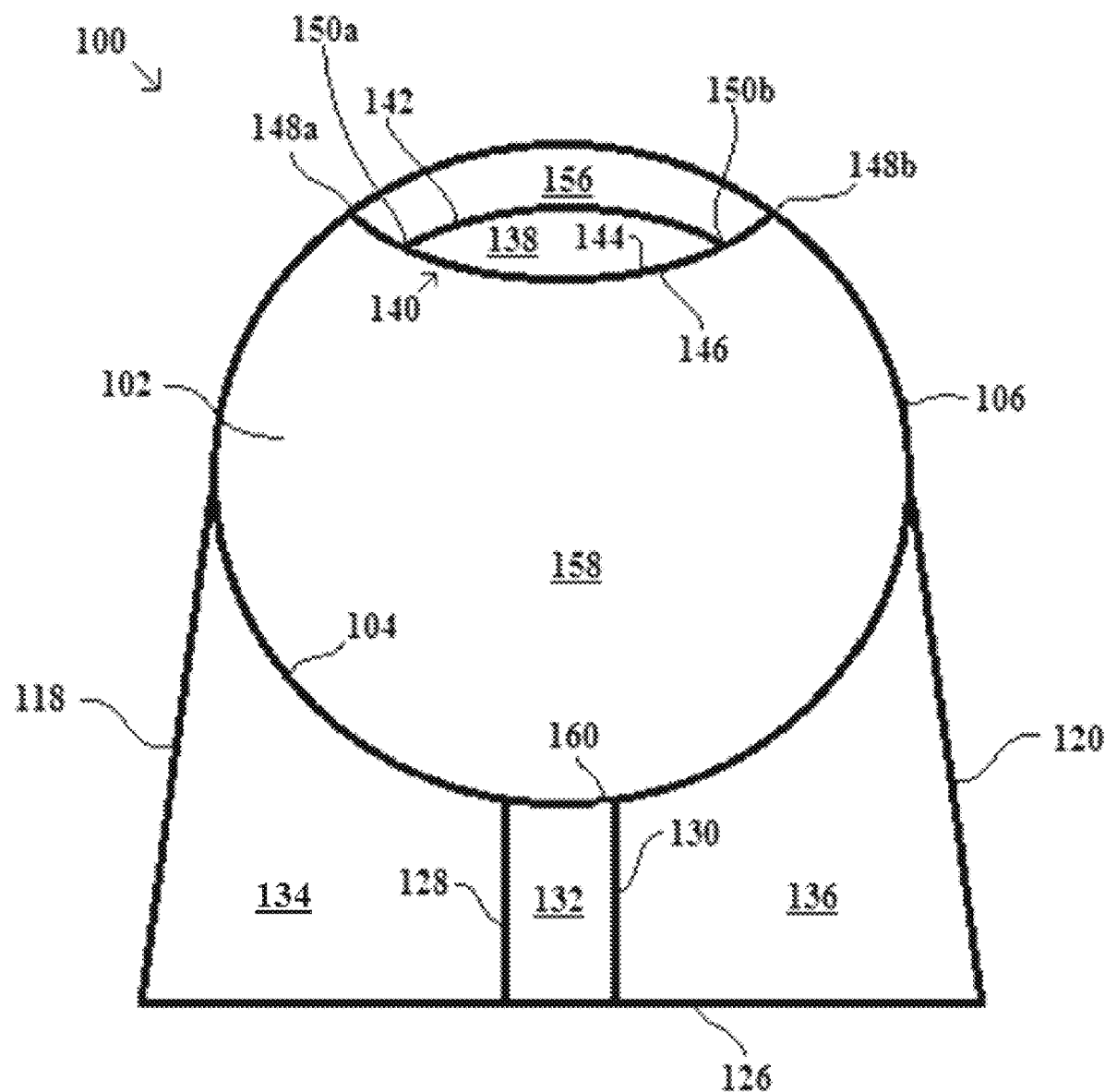
FIGS. 4A-4B: Cross-sectional views of an ocular ultrasound model segment.
Figure 4B:
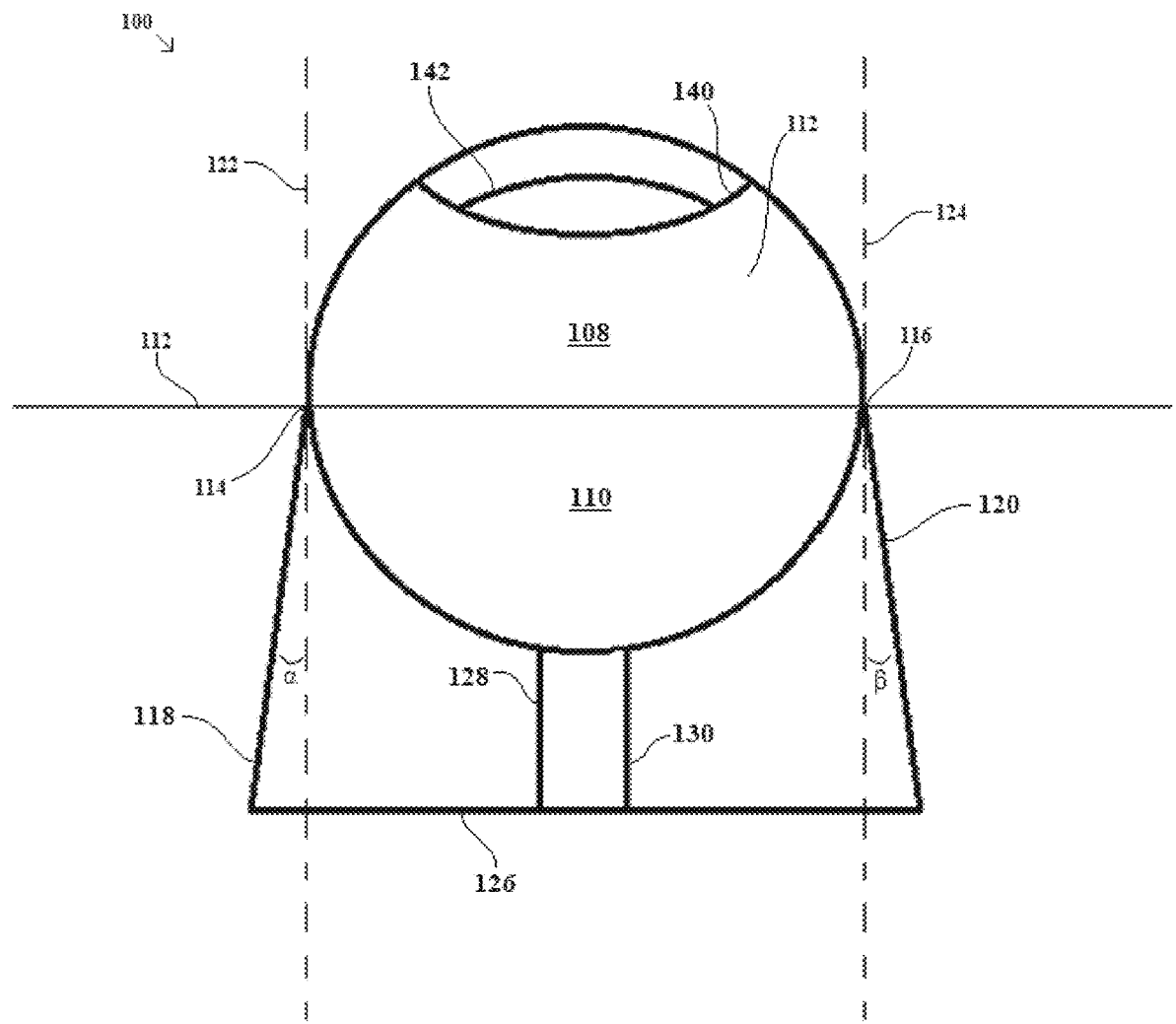

FIGS. 4A-4B depict a cross-section of a segment 100 of an ocular ultrasound model 10 of a normal eye. The segment 100 includes a globe 102 having an inner surface 104 and an outer surface 106. As shown in FIG. 4B, the globe 102 has an anterior section 108 and a posterior section 110 that are divided by an imaginery midline 112 which extends from a middle point 114 on a first side of the globe 102 to an opposing middle point 116 on a second side of the globe 102. The imaginery midline 112 divides the globe 102 in half. Two side walls 118, 120 extend from the middle points 114, 116 on the outer surface 106 of the globe 102, each at an angle α, β from a line 122, 124 tangent to the middle points 114, 116. In some embodiments, the angles α, β are equal. However, the angles α, β need not be equal. Each of the angles α, β may range independently from about 0° to about 20°. In some non-limiting examples, the angles α, β are each within a range of from about 5° to about 10°. However, other angles are possible.

The side walls 118, 120 each extend at the angle α, β to a bottom wall 126, which extends between the two side walls 118, 120. Two inner walls—a first inner wall 128 and a second inner wall 130—which, together, form a chamber 132 which provides a representation of the optic nerve in an ultrasound image, extend from the outer surface 106 of the globe 102 in the posterior section 110 to the bottom wall 126. This creates a first ultrasoundable chamber 134, between the first side wall 118 and the first inner wall 128 from the globe 102 to the bottom wall 126, and a second ultrasoundable chamber 136, between the second side wall 120 and the second inner wall 130 from the globe 102 to the bottom wall 126. The first and second ultrasoundable chambers 134, 136 aid in ultrasound viewing by reducing reflections.

Although the optic nerve chamber 132 is depicted in FIGS. 4A-4B by two inner walls 128, 130 which are parallel, it is understood that the inner walls 128, 130 need not be parallel or even substantially parallel. In fact, as described in more detail below, the inner walls 128, 130 may be made to have a varying diameter between them so as to simulate an abnormal optic nerve diameter under ultrasound. Moreover, the optic nerve chamber 132 may alternatively be formed by a cylindrical rod instead of parallel walls 128, 130. In some cases, a cylindrical rod may better simulate the optic nerve bundle on ultrasound.

Figure 5:
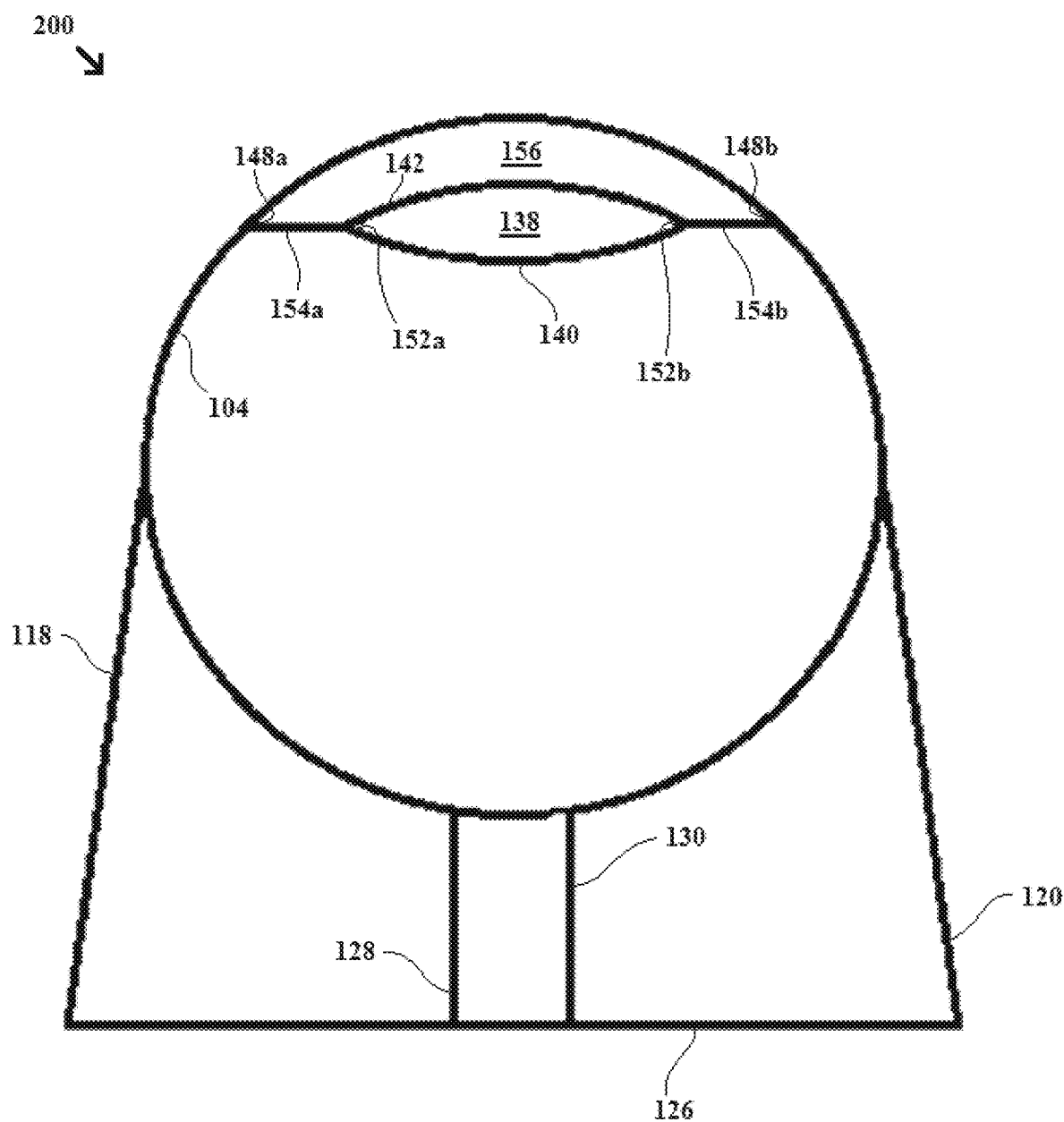
FIG. 5: Cross-sectional view of an alternative embodiment of an ocular ultrasound model segment.

Referring to FIGS. 4-5, the lens of the eye is represented by an enclosed lens chamber 138 in the anterior section 108 of the globe 102. In some embodiments, the lens chamber 138 is formed from a first arc 140 and a second arc 142. The first arc 140, which has an anterior surface 144 and a posterior surface 146, extends between two points 148a, 148b on the inner surface 104 of the globe 102, and the second arc 142 extends between two points 150a, 150b on the anterior surface 144 of the first arc 140. In one non-limiting example, one of the first arc 140 or second arc 142 is concentric with the globe 102. However, it is not necessary that either arc 140, 142 be concentric with the globe 102. Furthermore, the lens chamber 138 may be expanded in size in order to account for reflecting artifacts caused by the curved walls of the globe 102.

In other embodiments, as depicted in FIG. 5, neither the first arc 140 nor the second arc 142 extend to the globe 102. Rather, in some embodiments, the first and second arcs 140, 142 meet at both ends to form first and second lens chamber terminal points 152a, 152b, and thereby form the enclosed lens chamber 138. In such embodiments, the lens chamber 138 is supported by first and second chamber mounts 154a, 154b, which extend from the first and second lens chamber terminal points 152a, 152b to the globe 102. It is understood that other shapes and configurations are possible to represent the lens in an ultrasound image.

The iris of the eye is represented by an enclosed iris chamber 156 defined by the space within the globe 102 between the lens chamber 138 and the inner surface 104 of the globe 102 to the anterior side of the lens chamber 138. The shape of the iris chamber 156 may thus vary based on how the lens chamber 138 is formed. Accordingly, FIG. 4A depicts an iris chamber 156 defined by, in counter-clockwise order, the globe 102 from the second point 148b where the first arc 140 meets the inner surface 104 of the globe 102 to the first point 148a where the first arc 140 meets the inner surface 104 of the globe 102, the first arc 140 from the first point 148a to the point 150a, the second arc 142 from the point 150a to the point 150b, and the first arc 140 from the point 150b to the second point 148b on the inner surface 104 of the globe 102. Alternatively, FIG. 5 depicts a segment 200 having an iris chamber 156 defined by, in counter-clockwise order, the globe 102 from the second point 148b on the inner surface 104 to the first point 148a on the inner surface 104, the first lens chamber support mount 154a from the first point 148a to the first lens chamber terminal point 152a, the second arc 142 from the first lens chamber terminal point 152a to the second lens chamber terminal point 152b, and the second lens chamber support mount 154b from the second lens chamber terminal point 152b to the second point 148b on the inner surface 104 of the globe 102. It is understood that other shapes and configurations are possible to represent the iris on an ultrasound image.

Referring still to FIGS. 4-5, posterior to the lens chamber 138 within the globe 102 is a vitreous body chamber 158 which provides a representation of the vitreous body of the eye on an ultrasound image. The posterior wall 160 of the globe 102, which is the inner surface 104 of the globe 102 in the posterior section 110, provides a representation of the retina of the eye on an ultrasound image. Other shapes and configurations are possible to represent the vitreous body and the retinal on an ultrasound image.

To use under ultrasound, each of the chambers within the ocular ultrasound model, namely, the iris chamber 156, the lens chamber 138, the vitreous body chamber 158, the optic nerve chamber 132, the first ultrasoundable chamber 134, and the second ultrasoundable chamber 136 may be filled with a gelatinous substance prior to sealing or adhering the ocular ultrasound model together. The gelatinous substance can be any of a wide variety of substances including, but not limited to: gelatin, Jell-O, sugar-free Metamucil, agar, or combinations thereof. Suitable gelatinous substances include any substances, or combinations of substances, which allow for the ocular ultrasound model to provide a fair representation of a human eye under ultrasound. Once adhered together to form enclosed chambers filled with gel inside the model, the model is ready for use under ultrasound.

As seen in FIGS. 1A-1B, the top of the ocular ultrasound model 10, when sealed together, forms a dome 162, and the bottom of the ocular ultrasound model 10, when sealed together, may be a rectangular base 164. However, other shapes and configurations are entirely possible and encompassed within the present disclosure.

While it is advantageous to create 3D printed models which provide fair representations of a normal human eye under ultrasound, it is nonetheless important to provide similar models which provide representations under ultrasound of human eyes having abnormal pathologies, for the sake of training medical personnel to diagnose such pathologies with ultrasound. Thus, further provided herein are 3D printed ocular ultrasound models which provide representations under ultrasound of human eyes having abnormal pathologies. Such models are useful for training physicians and other emergency medicine personnel in the diagnosis of common eye injuries and diseases. FIGS. 6-13 depict cross-sectional views of non-limiting example ocular ultrasound models, similar to FIGS. 4-5, showing abnormal pathologies.

Figure 6A:
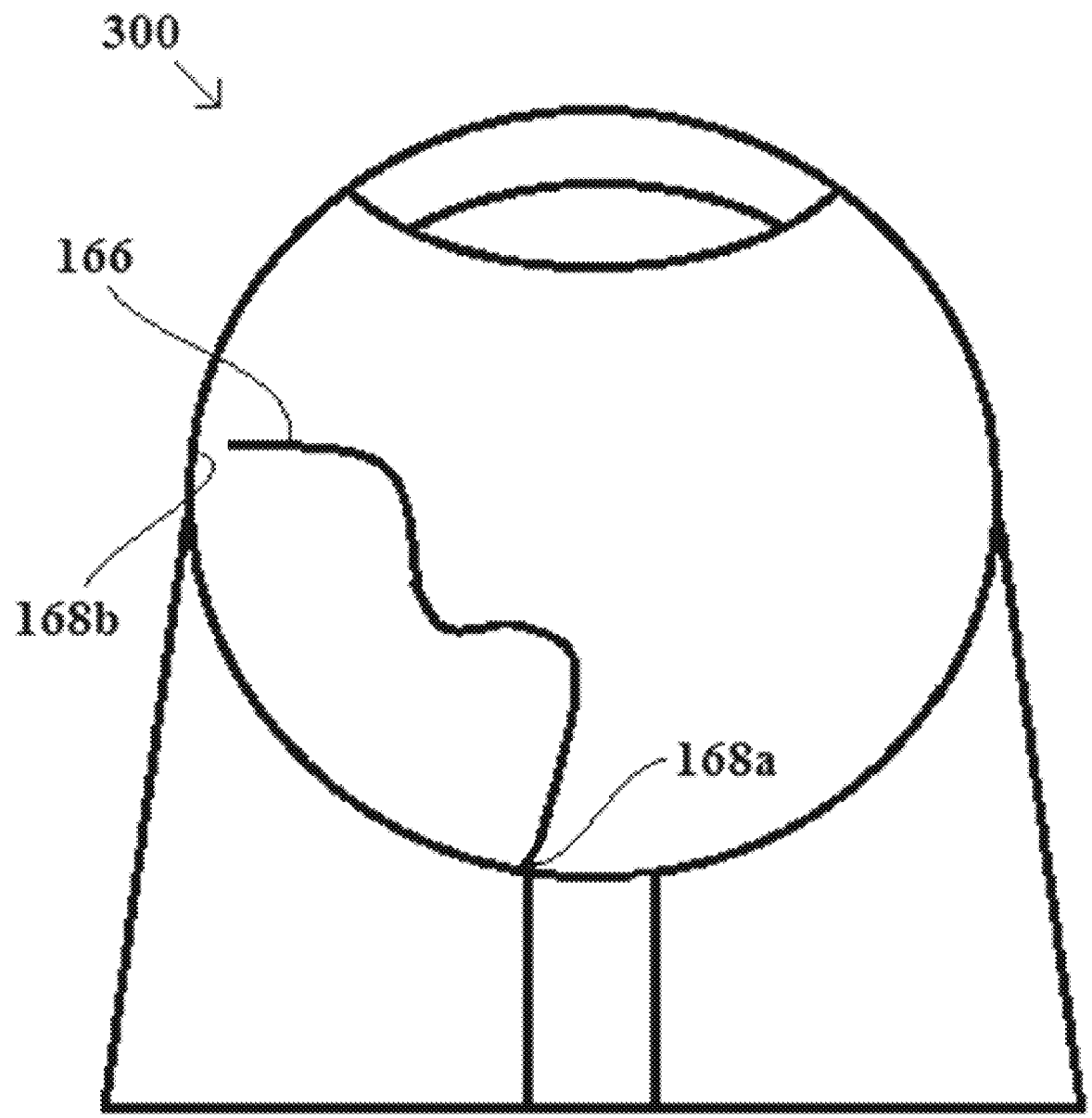
FIGS. 6A-6C: Cross-sectional view of an ocular ultrasound model providing a representation on an ultrasound image of a human eye having a detached retina (FIG. 6A), a photograph (FIG. 6B) of an example of such a model, and a photograph (FIG. 6C) of an ultrasound image of a real human eye with a retinal detachment.
Figure 6B:
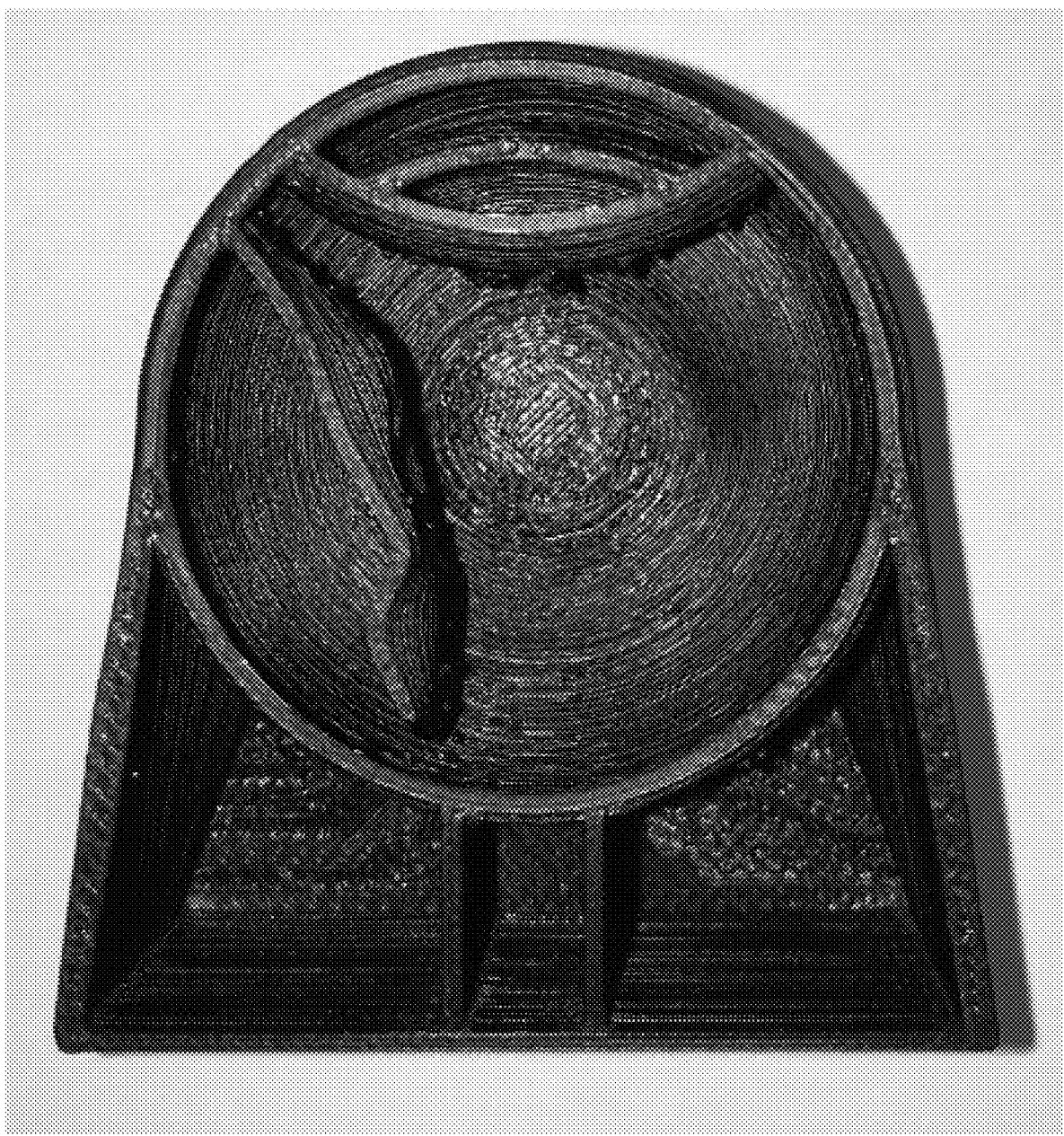
Figure 6C:
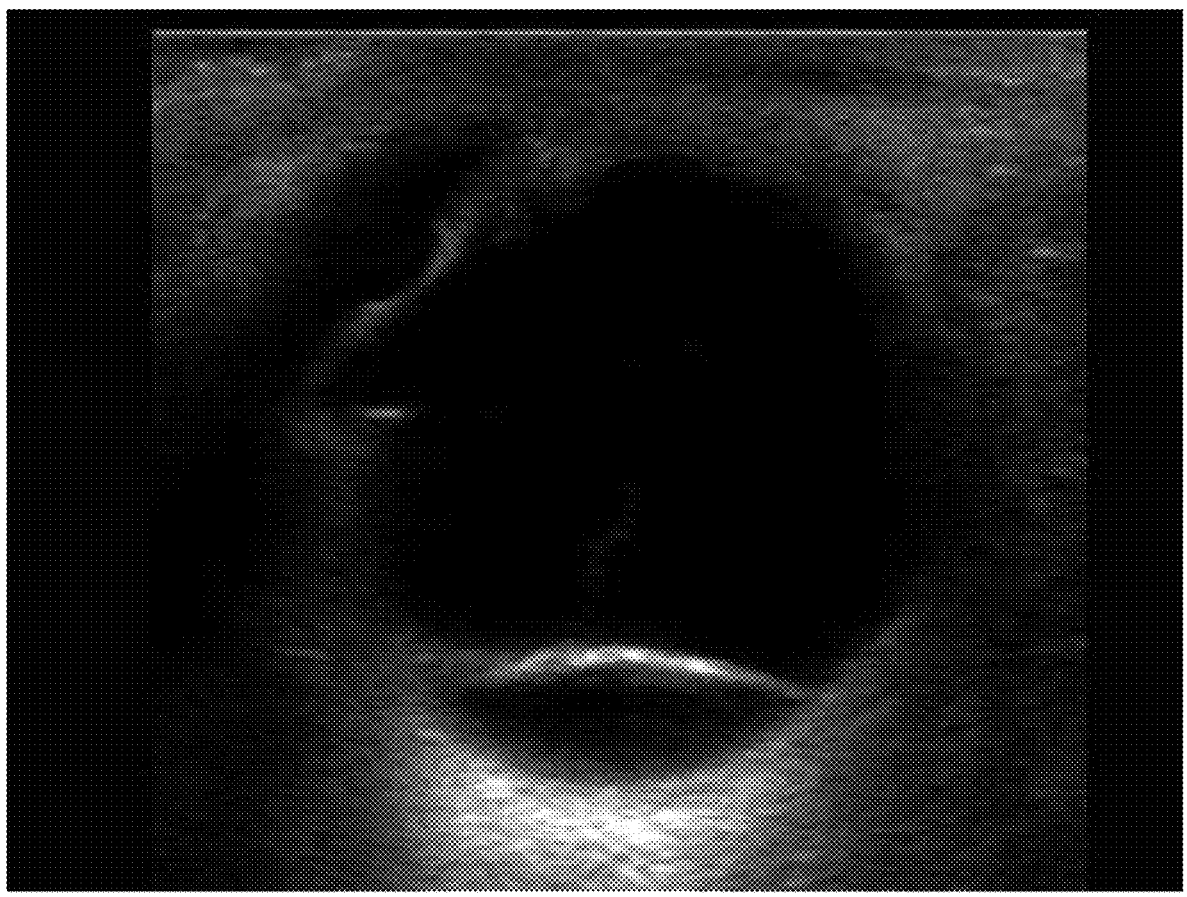

FIG. 6A depicts a cross-sectional view of a segment 300 of an ocular ultrasound model of an eye having a retinal detachment. As seen in FIG. 6A, the model of retinal detachment includes a curvy retinal wall 166 extending from a point on the inner surface 104 of the globe 102, referred to as the retinal attachment point 168*a*, to a space within the globe 102 near a second point 168*b* of the inner surface 104. The retinal wall 166 does not cross more than half the width of the globe 102. (This is because in a retinal detachment, a thick, hypoechoic undulating membrane in the posterior/lateral globe of the eye attaches to the ora serrata anteriorly and the optic nerve posteriorly.) FIG. 6B shows a photograph of an example segment 3D printed from ABS where a curvy wall is formed within the globe. FIG. 6C shows a photograph of an example ultrasound of a real human eye with a retinal detachment.

Figure 7:
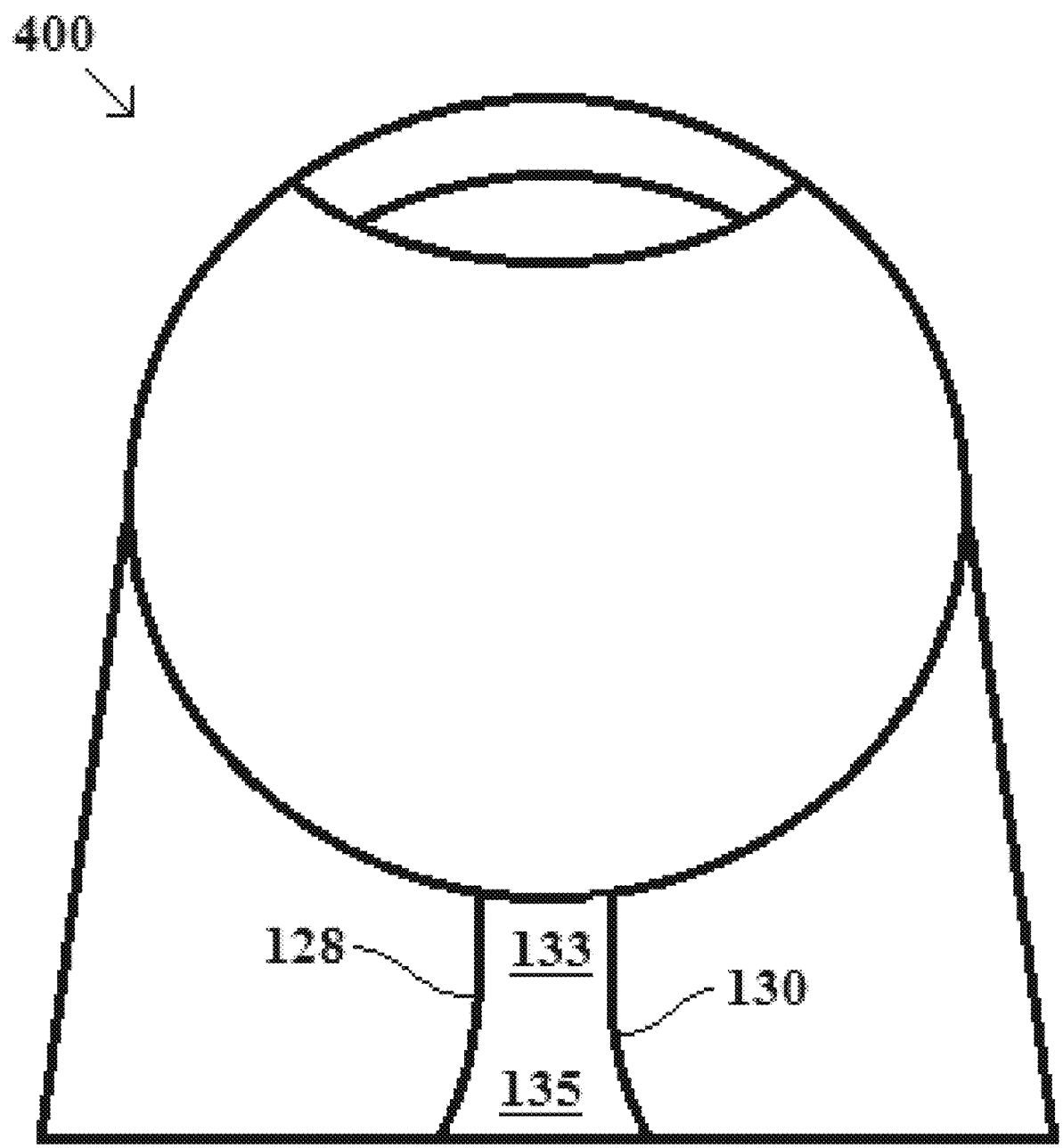
FIG. 7: Cross-sectional view of an ocular ultrasound model providing a representation on an ultrasound image of a human eye having an increased optic nerve diameter.

FIG. 7 depicts a cross-sectional view of a segment 400 an ocular ultrasound model of an eye having increased optic nerve diameter. As seen in FIG. 7, the optic nerve chamber 132 has a narrower section 133 and a wider section 135. In one non-limiting example, the narrower section has a diameter of about 3 mm, and the wider section 135 has a diameter of about 7-8 mm. Such a model can be made by 3D printing a portion of the inner walls 128, 130 with a subtle curve.

Figure 8:
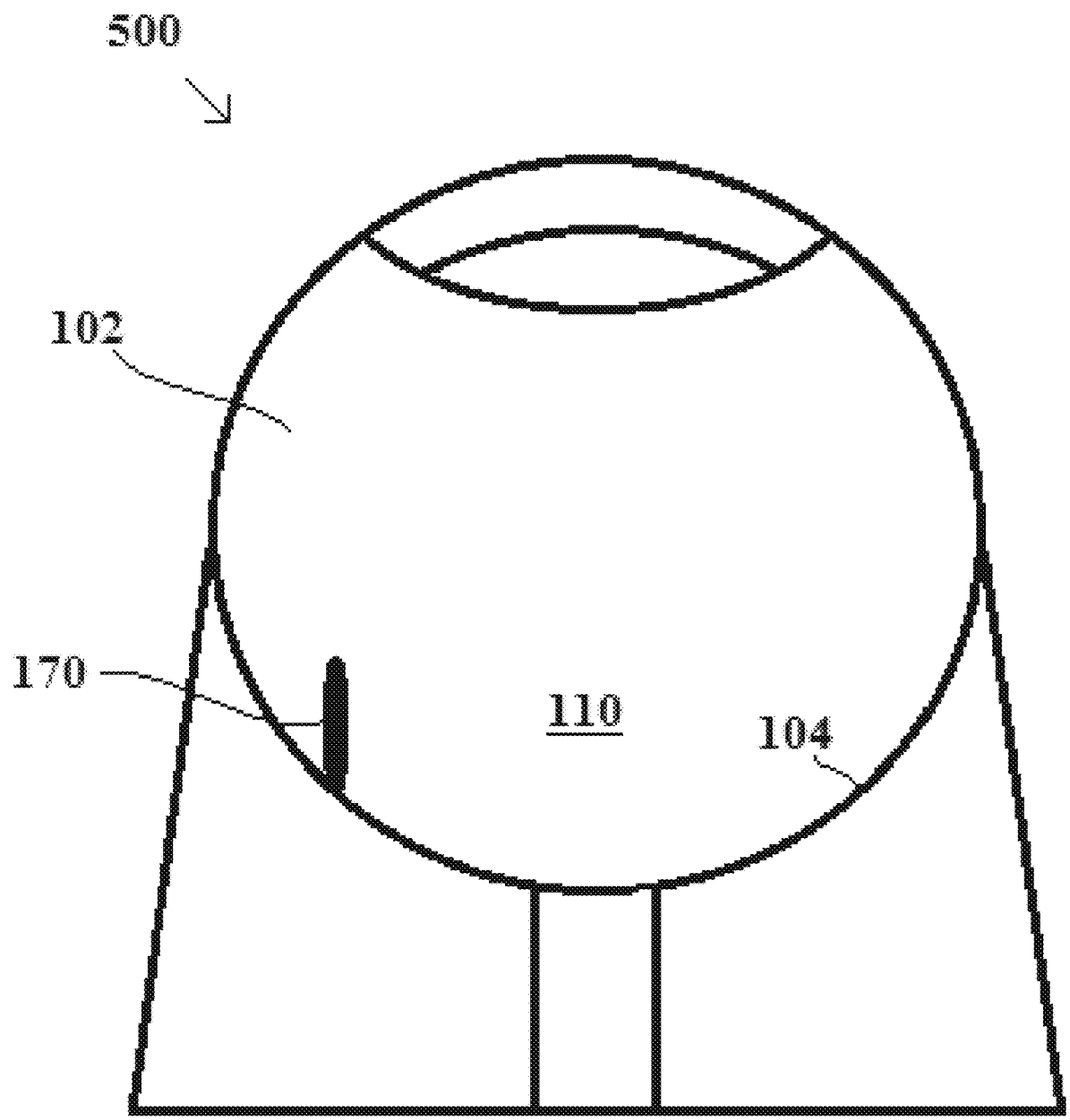
FIG. 8: Cross-sectional view of an ocular ultrasound model providing a representation on an ultrasound image of a human eye having an intraocular foreign object.

FIG. 8 depicts a cross-sectional view of a segment 500 of an ocular ultrasound model of an eye having an intracular foreign body. As seen in FIG. 8, a dense foreign body wall 170 extends from the inner surface 104 of the globe 102 at an arbitrary location. FIG. 8 depicts the foreign body wall 170 in the posterior section 110 of the globe 102, but the foreign body wall 170 need not be in the posterior section 110.

Figure 9A:
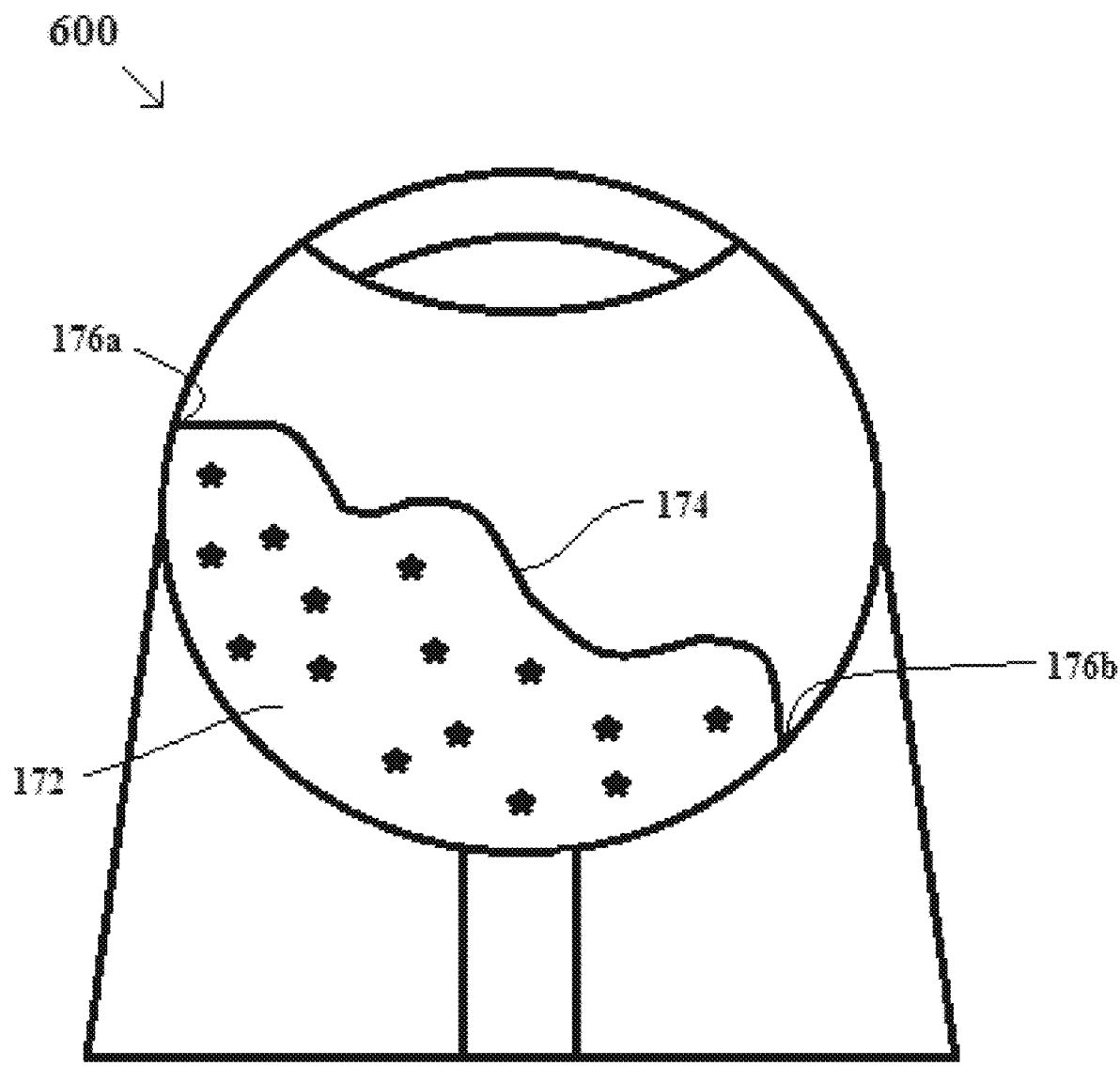
FIGS. 9A-9B: Cross-sectional view of an ocular ultrasound model providing a representation on an ultrasound image of a human eye having a vitreous hemorrhage (FIG. 9B), and an ultrasound image of a real human eye with a vitreous hemorrhage (FIG. 9B).
Figure 9B:

FIG. 9A depicts a cross-sectional view of a segment 600 of an ocular ultrasound model of an eye a vitreous hemorrhage, which is the extravasation of blood into the areas in and around the vitreous humor of the eye. As seen in FIG. 9A, the cross section of segment 600 has a speckled area 172 within the globe 102 defined by a curvy wall 174 extending between two points 176*a*, 176*b* on the inner surface 104 of the globe 102. The curvy wall 174 crosses over more than half the width of the globe 102. The speckled area 172 can be made by adding glitter into the area 172 of the model after printing. FIG. 9B depicts an ultrasound image of a real human eye with a vitreous hemorrhage.

Figure 10:
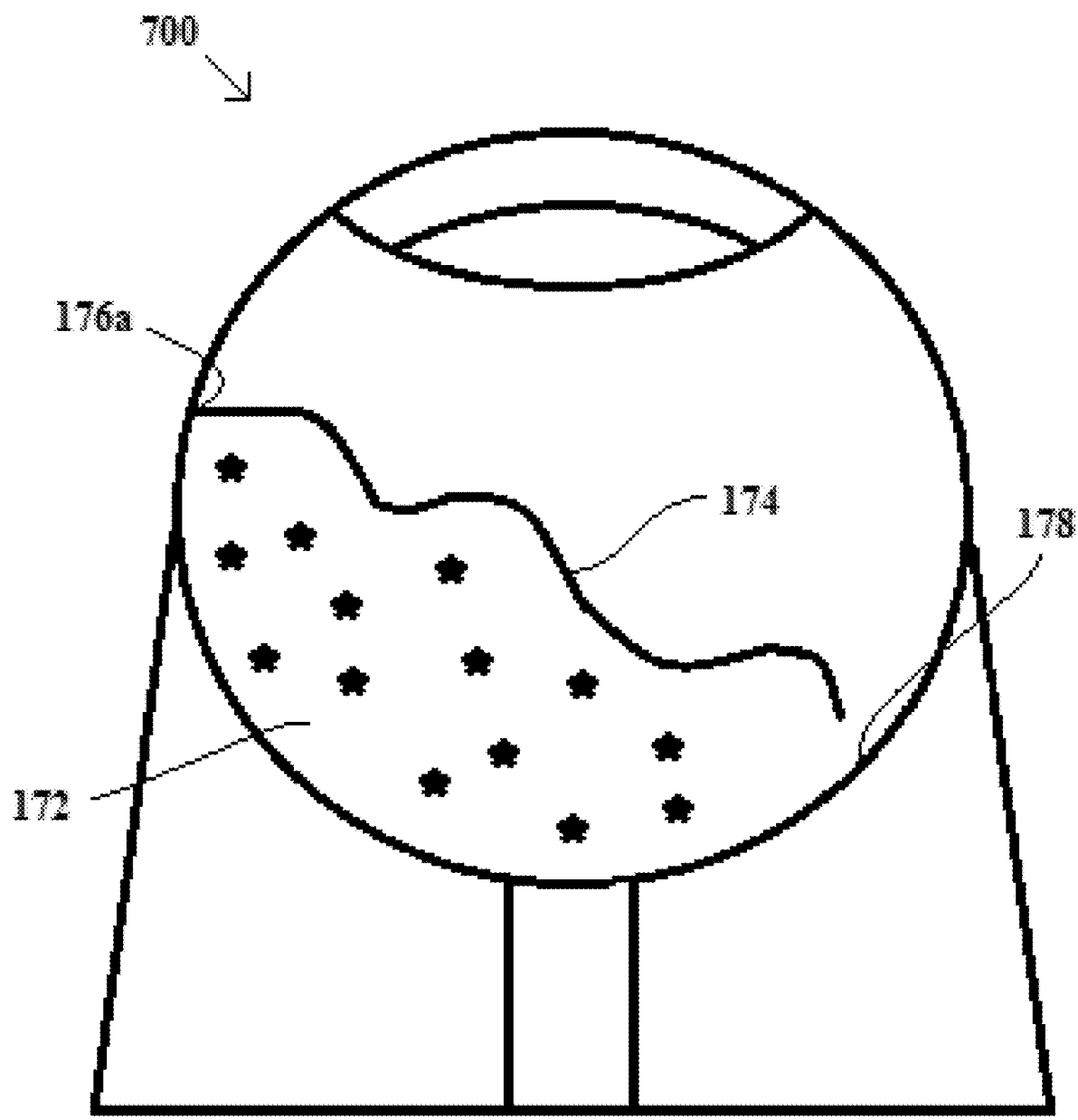
FIG. 10: Cross-sectional view of an ocular ultrasound model providing a representation on an ultrasound image of a human eye having a vitreous detachment.

FIG. 10 depicts a cross-sectional view of an ocular ultrasound model of an eye having a vitreous detachment. As seen in FIG. 10, the segment 700 has a speckled area 172 defined by a curvy wall 174 that extends from first point 176*a* to a space near, but not touching, a point 178 on the inner surface 104 of the globe 102. Thus, the segment 700 includes an opening between the curvy wall 174 and the point 178. The curvy wall 174 crosses over more than half the width of the globe 102.

Figure 11:
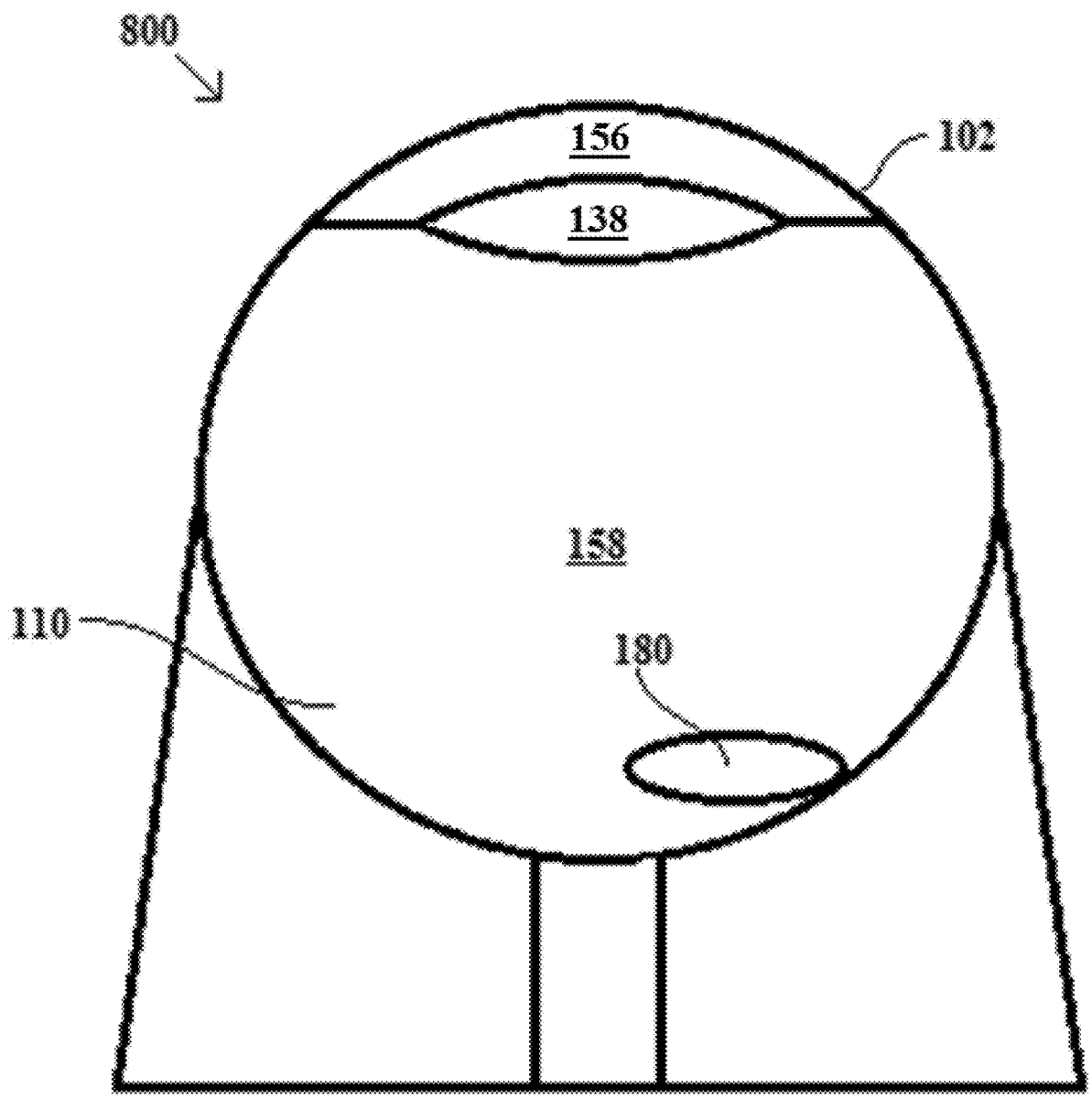
FIG. 11: Cross-sectional view of an ocular ultrasound model providing a representation on an ultrasound image of a human eye having a detached lens.

FIG. 11 depicts a cross-sectional view of a segment 800 of an ocular ultrasound model of an eye having a dislocated lens. As seen in FIG. 11, a dislocated lens chamber 180 is formed in the vitreous body chamber 158 in the posterior section 108 of the globe 102. For purposes of illustration, the segment 800 also includes an alternative embodiment of the lens chamber 138 and iris chamber 156.

Figure 12:
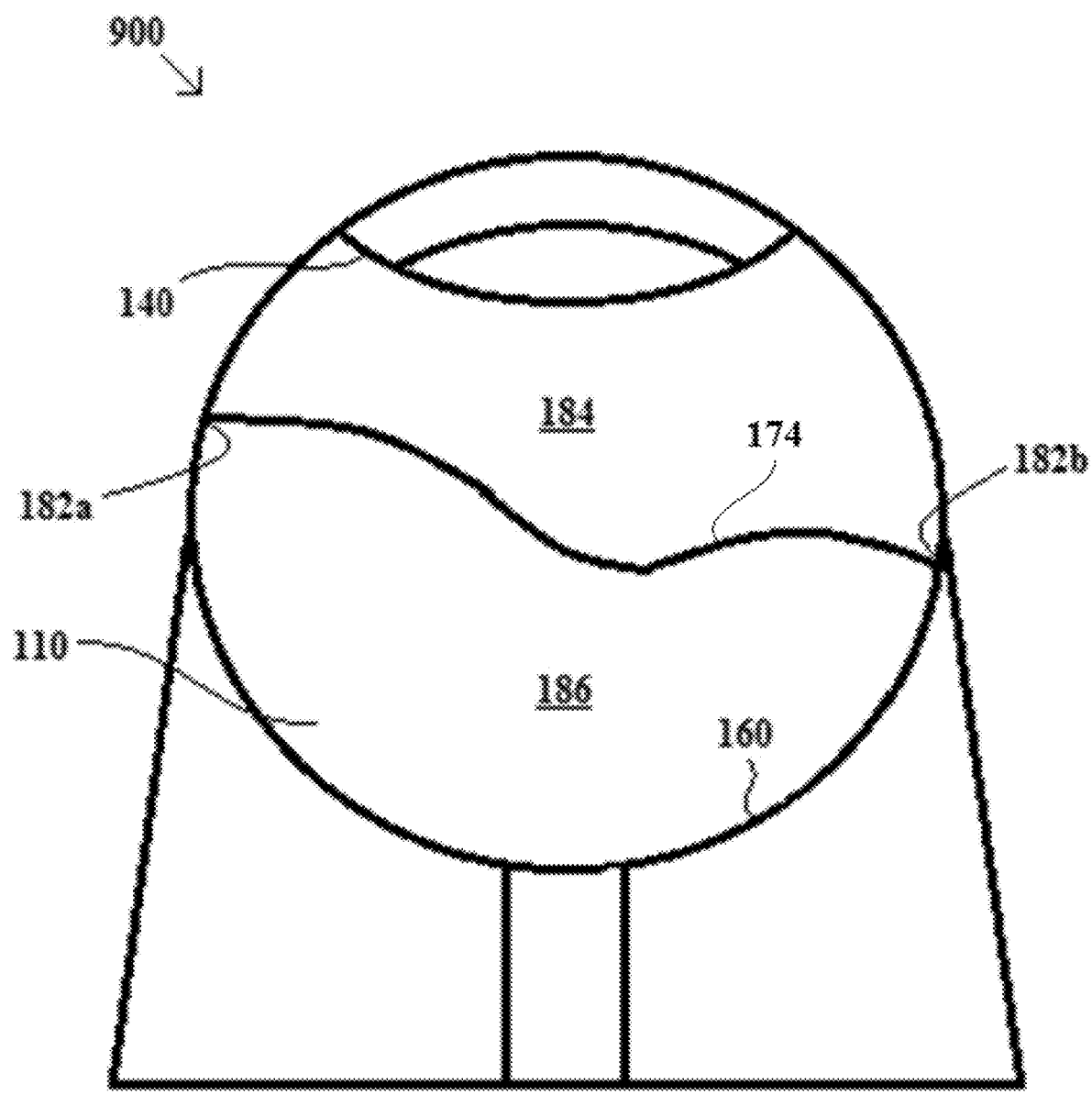
FIG. 12: Cross-sectional view of an ocular ultrasound model providing a representation on an ultrasound image of a human eye having a ruptured globe.

FIG. 12 depicts a cross-sectional view of a segment 900 of an ocular ultrasound model of an eye having a ruptured globe. Globe rupture is a major ophthalmologic emergency that typically requires surgical intervention. Ultrasound findings of a ruptured globe generally include a decrease in the size of the globe, a collapse of the anterior chamber, and buckling of the sclera. This is represented in the model by a curvy wall 174 extending from a first point 182*a* on the inner surface 104 of the globe 102 to a second point 182*b* on the inner surface of the globe 102, where the curvy wall 174 effectively creates a reduced globe space 184 between the first arc 140 and the curvy wall 174 that is less in volume than the space 186 between the curvy wall 174 and the posterior wall 160 of the globe 102.

Figure 13:
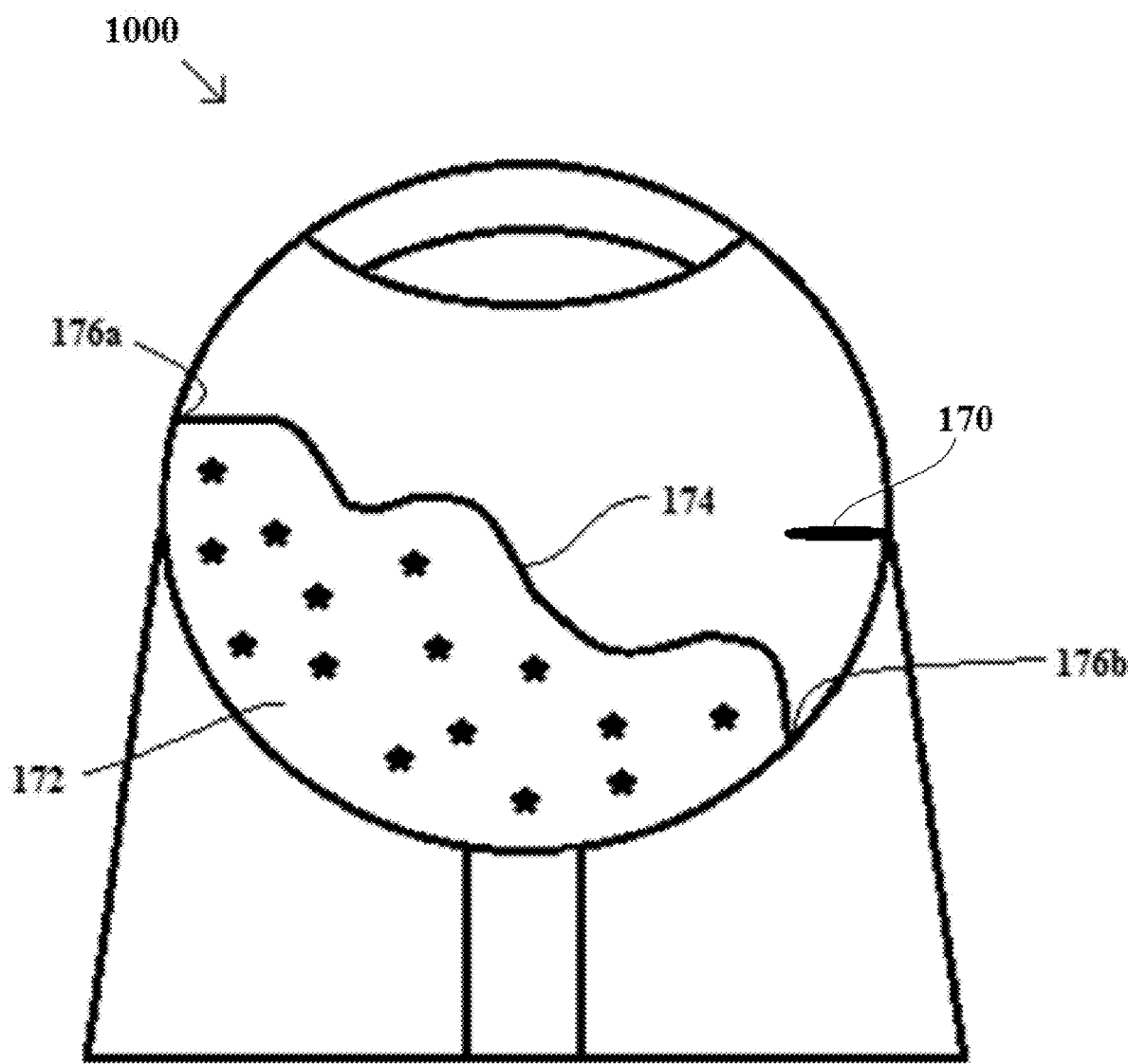
FIG. 13: Cross-sectional view of an ocular ultrasound model providing a representation on an ultrasound image of a human eye having a vitreous hemorrhage and an intraocular foreign object.

FIG. 13 depicts a cross-sectional view of a segment 1000 of an ocular ultrasound model of an eye having multiple abnormal pathologies, namely a vitreous hemorrhage and a foreign body. As seen in FIG. 13, this model has a speckled area 172 underneath a curvy wall 174 extending from point 176*a* to point 176*b*, and further includes a foreign body wall 170 within the globe 102.

As described in the examples herein, the ocular ultrasound models may be 3D printed out of a suitable plastic material. Any plastic material is suitable so long as the printing parameters result in a printed model that provides a fair representation of a human eye under ultrasound. Non-limiting examples of plastic materials include ABS, PLA, nylon (polyamide), polyvinyl alcohol (PVA), polyethylene terephthalate (PET), or polyethylene trimethylene terephthalate (PETT). In some embodiments, the ocular ultrasound model is composed of acrylonitrile butadiene styrene (ABS). In other embodiments, the ultrasound model is composed of polylactic acid (PLA). In some embodiments, the ultrasound model is made entirely of a single plastic material. As described in the examples herein, ultrasoundable ocular models were 3D-printed from ABS using a variety of printing parameters, and it was determined that a nozzle temperature of about 240° C. and bed temperature of about 125° C., along with a layer height of about 0.2 mm, a fill of 100%, and a speed of about 35 mm/s provide optimal results. A fill of 100% eliminates possible airspace between layers of material. Higher temperatures may result in bubbles formed in the plastic. A thinner wall generally allows for more clarity in the ultrasound results. In some embodiments, the walls of the ocular ultrasound model are from about 0.10 mm to about 0.25 mm thick, or from about 0.15 mm to about 0.22 mm thick. However, the ocular ultrasound model may be 3D-printed from other materials using other printing parameters. As is common in 3D printing, the model sections can be printed on a suitable support or substrate which can can peeled off of the printed object. This can result in a rough surface (as seen in FIG. 1B), which may be sanded or otherwise smoothed if desired.

In some embodiments, the ocular ultrasound models are 3D printed from a flexible or soft material to make the models more realistic feeling, thereby improving the user's experience learning from the ocular ultrasound models.

Figure 22:
FIG. 22: Photograph showing a 3D printed ocular ultrasound models that is soft and flexible.

Advantageously, soft models arem ore realistic to provide higher immersion, provide better contact with an ultrasound probe and gel to produce clear and wider imaging, and require the use of less gel. FIG. 22 shows a photograph of a 3D printed ocular ultrasound model that is soft and flexible.

Figure 23:
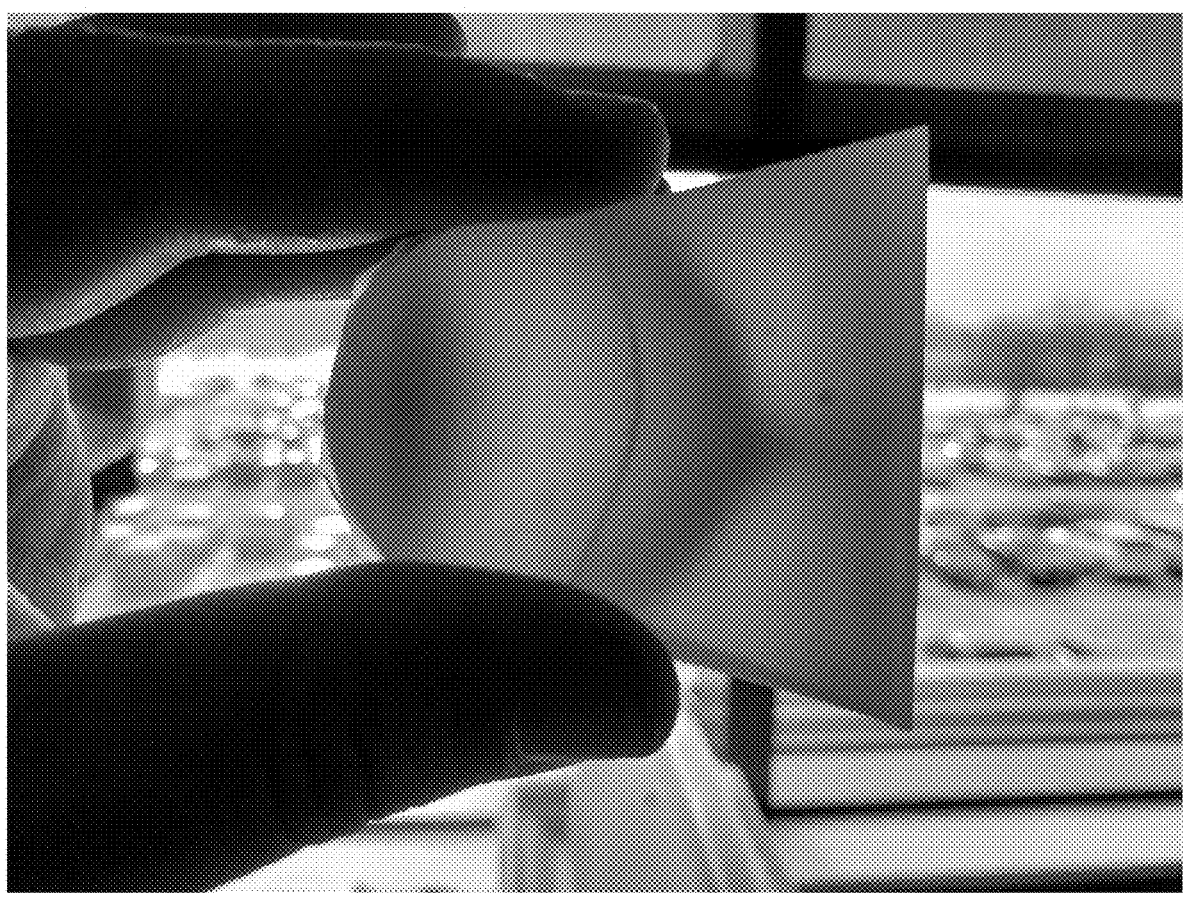
FIG. 23: Photograph showing a 3D printed ocular ultrasound model that is translucent.

Additionally, the ocular ultrasound models can be made to be translucent. FIG. 23 shows a photograph of a 3D printed ocular ultrasound model that is translucent. Translucent ocular ultrasound models may better help learners understand the anatomy for the eye, and understand the pathologies of the ocular ultrasound models to better read ultrasound imaging. Furthermore, manufacturing translucent ocular ultrasound models allows for seeing any defects, such as bubbles, more easily, which provides for better quality control. In other embodiments, the ocular ultrasound models are made to be opaque.

Extrusion processes inherently result in some bubbling in the plastic as it extrudes, and microscopic air gaps where the plastic is joining. However, the effects of these bubbles and air gaps can be minimized by printing parameters and techniques. For example, a polyjet printer can be used for improved results. Polyjet printing is a printing technique that sprays microscopically thin polymer layers as it builds up the print, while allowing for an exponentially higher print resolution. Polyjet printing can greatly limit the introduction of airspaces in the model, while at the same time allowing for the wall thickness to be reduced and thereby achieving an optimal balance of structural integrity and ultrasound scan clarity. However, any 3D printer can be used, including fused deposition modeling (FDM) printers. It is understood that the optimal printing parameters may vary depending on the type of 3D printer being used.

Figure 14A:
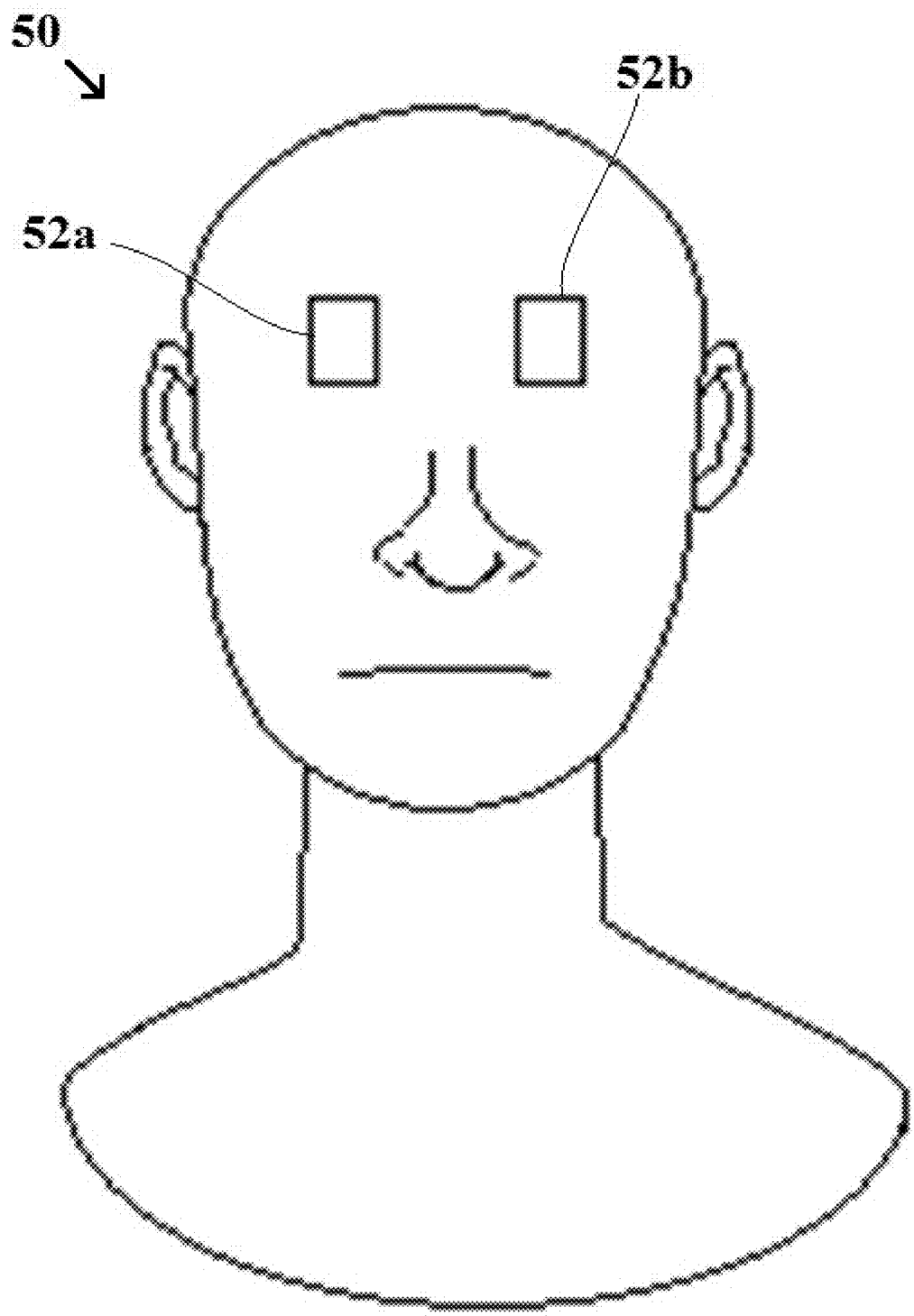
FIGS. 14A-14E: Illustrations of ocular ultrasound training simulators with empty eye sockets (FIGS. 14A, 14C) and with ocular ultrasound models in the eye sockets (FIGS. 14B, 14D).
Figure 14B:
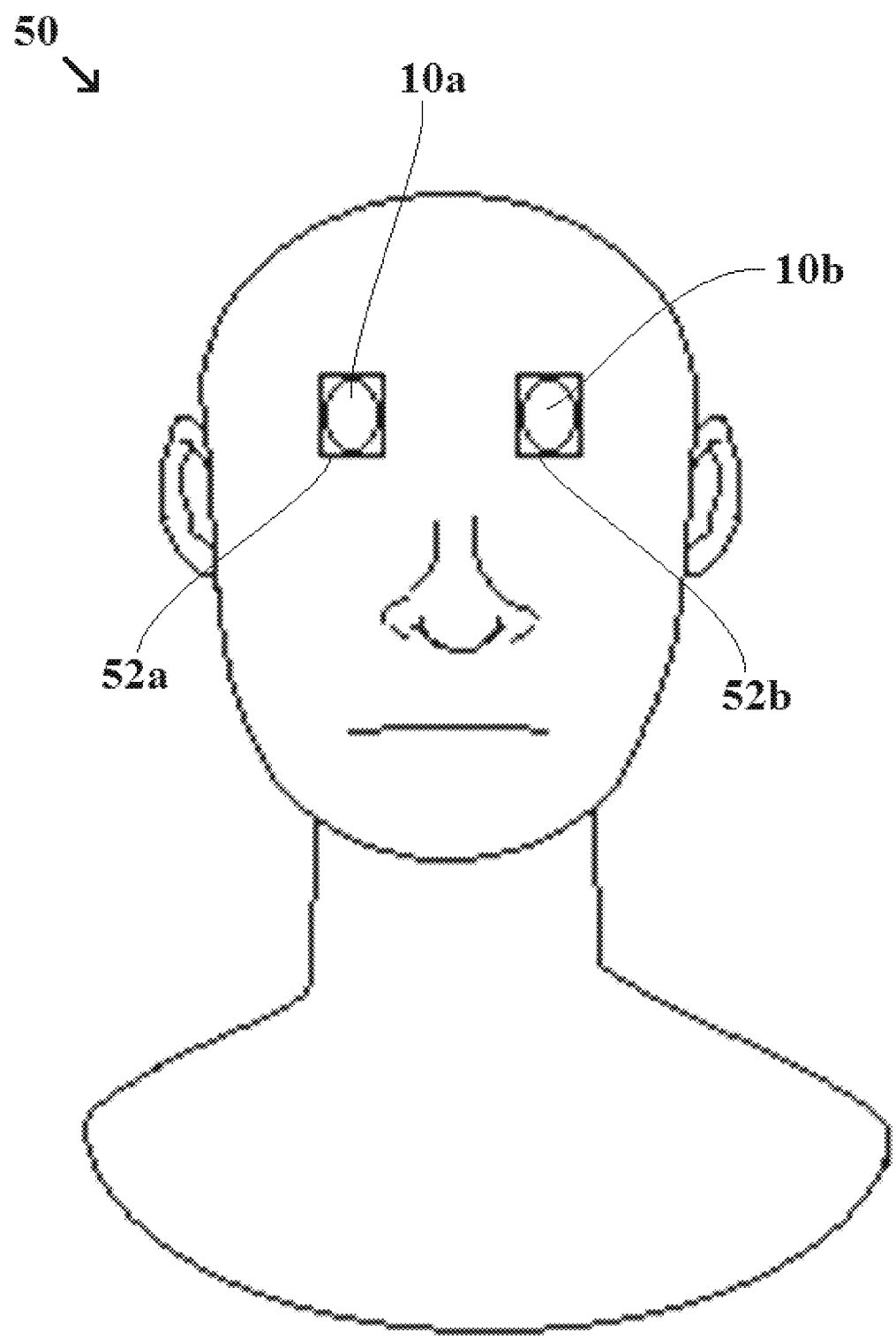

Further provided is a training simulator that can be used with the ocular ultrasound models. FIGS. 14A-14B depict a non-limiting example of an ocular ultrasound training simulator 50. The ocular ultrasound training simulator 50 is a representation of a human head, made of silicon or other suitable material, having two empty eye sockets 52*a*, 52*b* in the place of eyes. The empty eye sockets 52*a*, 52*b* are each configured to receive an ocular ultrasound model 10*a*, 10*b*. To use, two ocular ultrasound models 10*a*, 10*b* are inserted into the sockets 52*a*, 52*b*, and a person studying or practicing ocular ultrasound then takes ultrasound images of the ocular ultrasound models 10*a*, 10*b* while inserted into the sockets 52*a*, 52*b*. Different pathologies may be inserted at the same time, i.e., one ocular model 10*a* in the simulator 50 may represent a normal eye while the other ocular model 10*b* may represent an abnormal eye having, for instance, a foreign object. In this manner, the user can practice taking ocular ultrasounds on a life-like model. Having the ability to practice ocular ultrasound more easily and effectively may increase learners' comfort skill level.

Figure 14C:
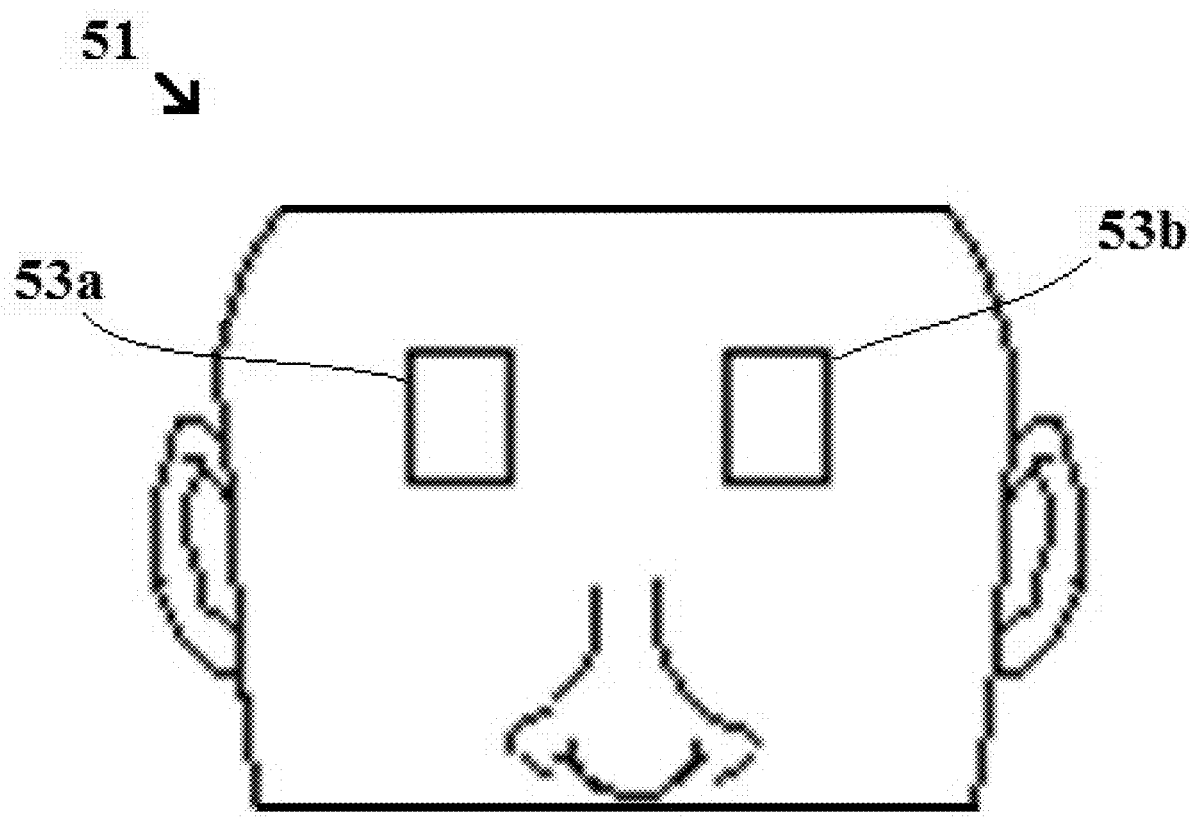
Figure 14D:
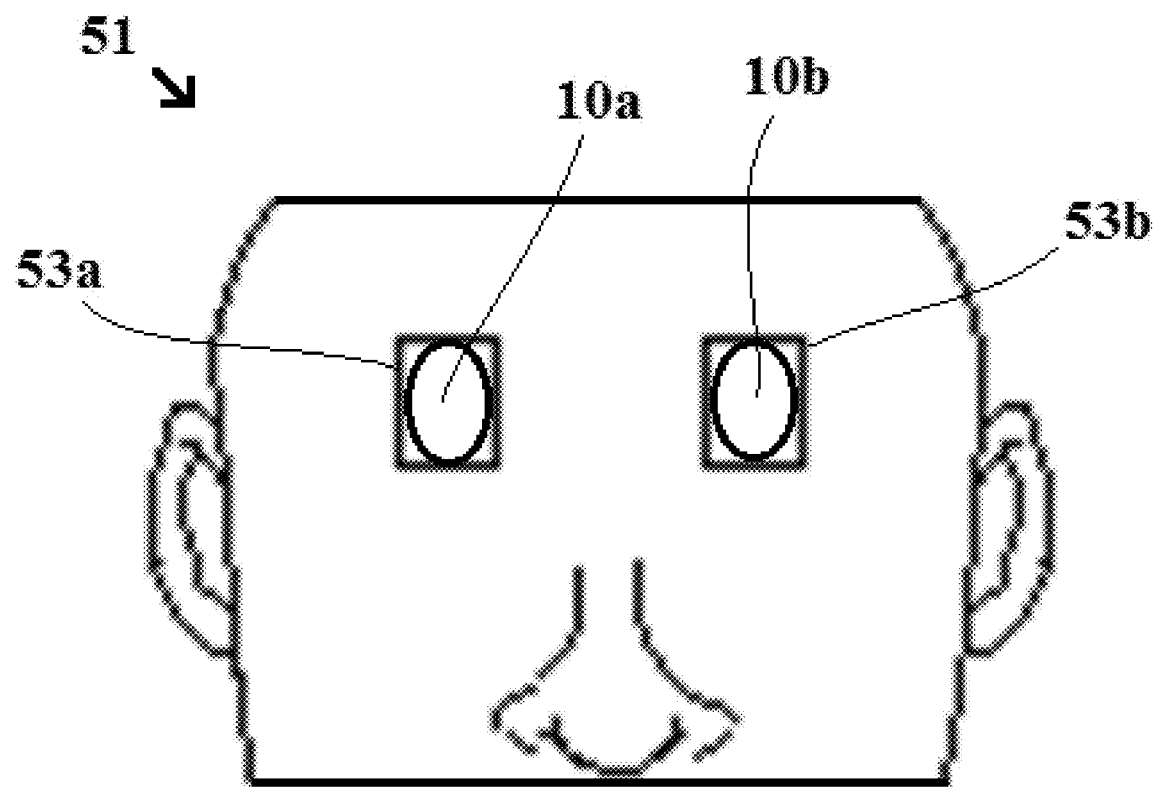

In an alternative embodiment, as depicted in FIGS. 14C-14D, an ocular ultrasound training simulator 51 is a representation of a human head only from the middle of the forehead to the bottom of the nose, so as to save on the cost of materials. The simulator 51 is used in the same manner as the simulator 50 depicted in FIGS. 14A-14B; that is, two ocular ultrasound moduels 10*a*, 10*b* are inserted into the sockets 53*a*, 53*b*, and a person studying or practicing ocular ultrasound then takes ultrasound images of the ocular ultrasound models 10*a*, 10*b* while inserted into the sockets 53*a*, 53*b*.

Figure 14E:
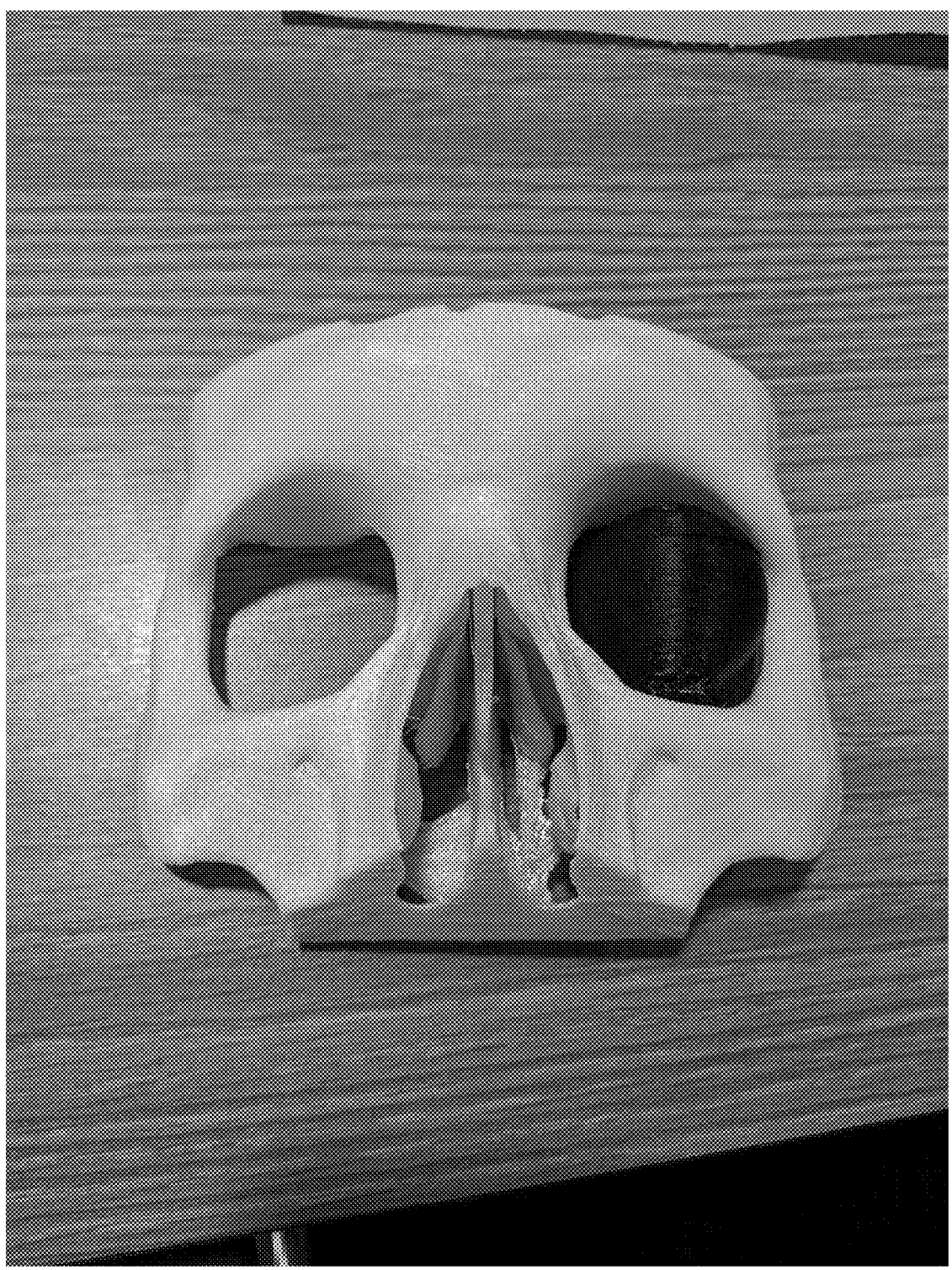

FIG. 14E shows a photograph of an alternative embodiment of an ocular ultrasound training simulator. This embodiment of an ocular ultrasound training simulator is in the form of an anatomically faithful faceplate that stabilizes the ocular ultrasound models so that a user does not need to use their hands, and helps the user position their probe and hands during imaging. The eye sockets may hold ultrasound gel during imaging. The photograph in FIG. 14E shows the faceplate having one eye socket empty and one eye socket filled with an ocular ultrasound model.

It is understood that the ocular ultrasound training simulator may further include other anatomical models for training purposes. For example, the ocular ultrasound training simulator may include more than merely a head, and for example may include an ultrasoundable representation of a torso.

The ocular ultrasound training simulator and ocular ultrasound models may be embodied in the form of a kit or kits. A non-limiting example of such a kit is a kit comprising an ocular ultrasound training simulator and two or more ocular ultrasound models in separate containers, where the containers may or may not be present in a combined configuration. Many other kits are possible, such as kits further including other anatomical models. In some embodiments, the kit includes ocular ultrasound models of both normal and abnormal pathology. In some embodiments, the kit includes ocular ultrasound models of each of a normal eye, retinal detachment, lens dislocation, vitreous hemorrhage, foreign body, globe rupture, and increased optic nerve diameter. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

Example 1

Figure 15:
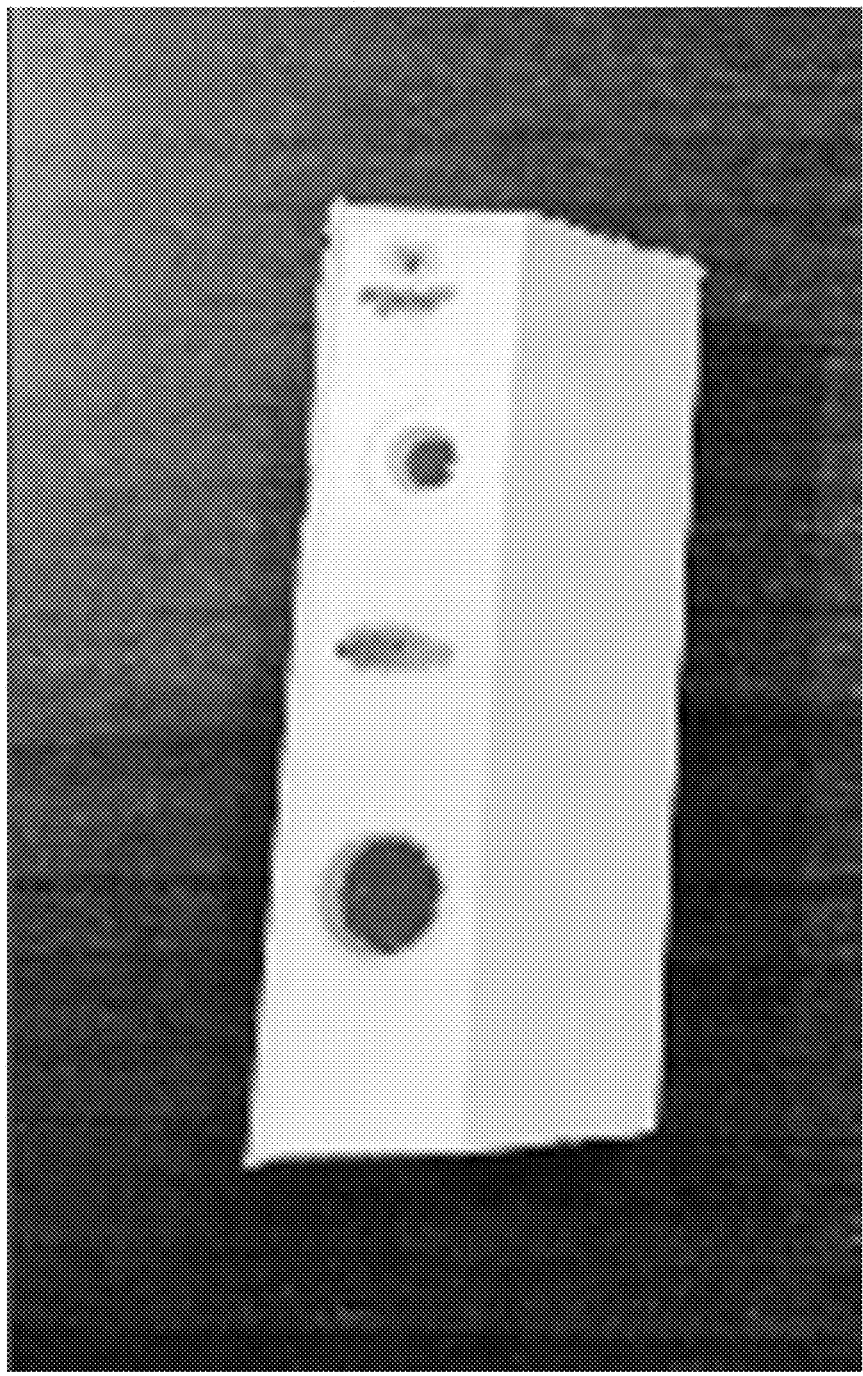
FIG. 15: Photograph of an example 3D printed model printed from PLA using default PLA printer settings.

A model was 3D printed out of PLA with an FDM printer using default PLA settings. The layer height was 0.25 mm, the shell was 1 mm, the fill was 20%, the speed was 80 mm/s, the nozzle temperature was 225° C., and the bed temperature was 70° C. The resulting printed model is pictured in FIG. 15. The ultrasound scanner did not scan through the model from the intended direction. It was, however, noted that the scanner did work while scanning from the print bed surface. This surface was printed slower. Without wishing to be bound by theory, it is believed that air bubbles in the plastic were a factor.

Example 2

Figure 16:
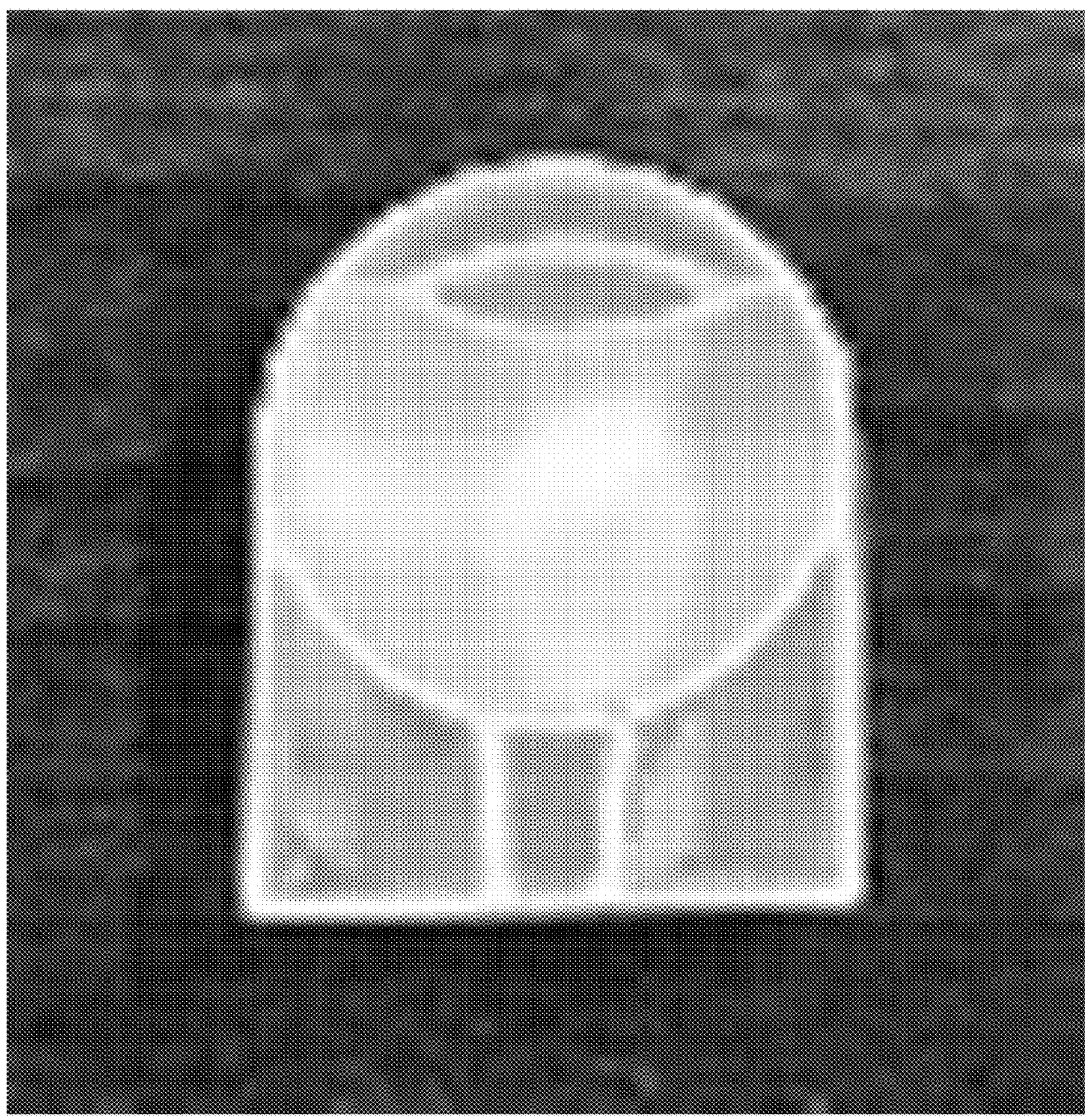
FIG. 16: Photograph of an example 3D printed model printed from PLA using a slightly reduced nozzle temperature.

A model was 3D printed out of PLA with an FDM printer using a layer height of 0.2 mm, a shell of 0.5 mm, a fill of 23%, a speed of 35 mm/s, a nozzle temperature of 200° C. (reduced from Example 1 in order to decrease the bubbles in the plastic), and a bed temperature of 70° C. The resulting printed model is pictured in FIG. 16. However, the ultrasound scanner still could not scan through from the intended direction.

Example 3

Figure 17:
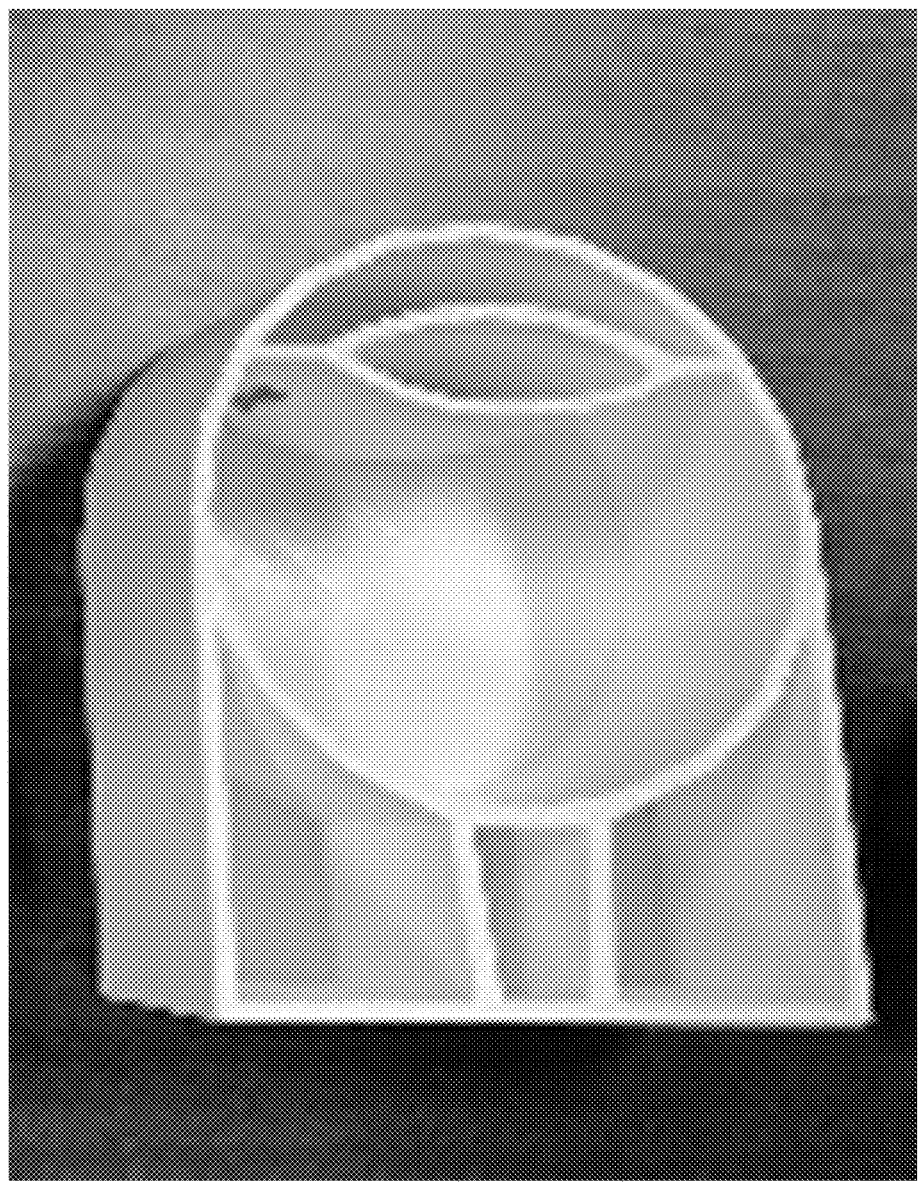
FIG. 17: Photograph of an example 3D printed model printed from PLA using a slightly reduced nozzle temperature, and printed on a larger scale.

A model was 3D printed out of PLA with an FDM printer using a layer height of 0.2 mm, a shell of 0.5 mm, a fill of 23%, a speed of 35 mm/s, a nozzle temperature of 200° C. (reduced from Example 1 in order to decrease the bubbles in the plastic), and a bed temperature of 70° C. The model was generically scaled. The printed model is pictured in FIG. 17 The model was not successful. The wall thickness prevented the scan from penetrating the walls. The larger scale allowed for the observation that low fill % was allowing for air gaps to be created between the shell walls.

Example 4

Figure 18:
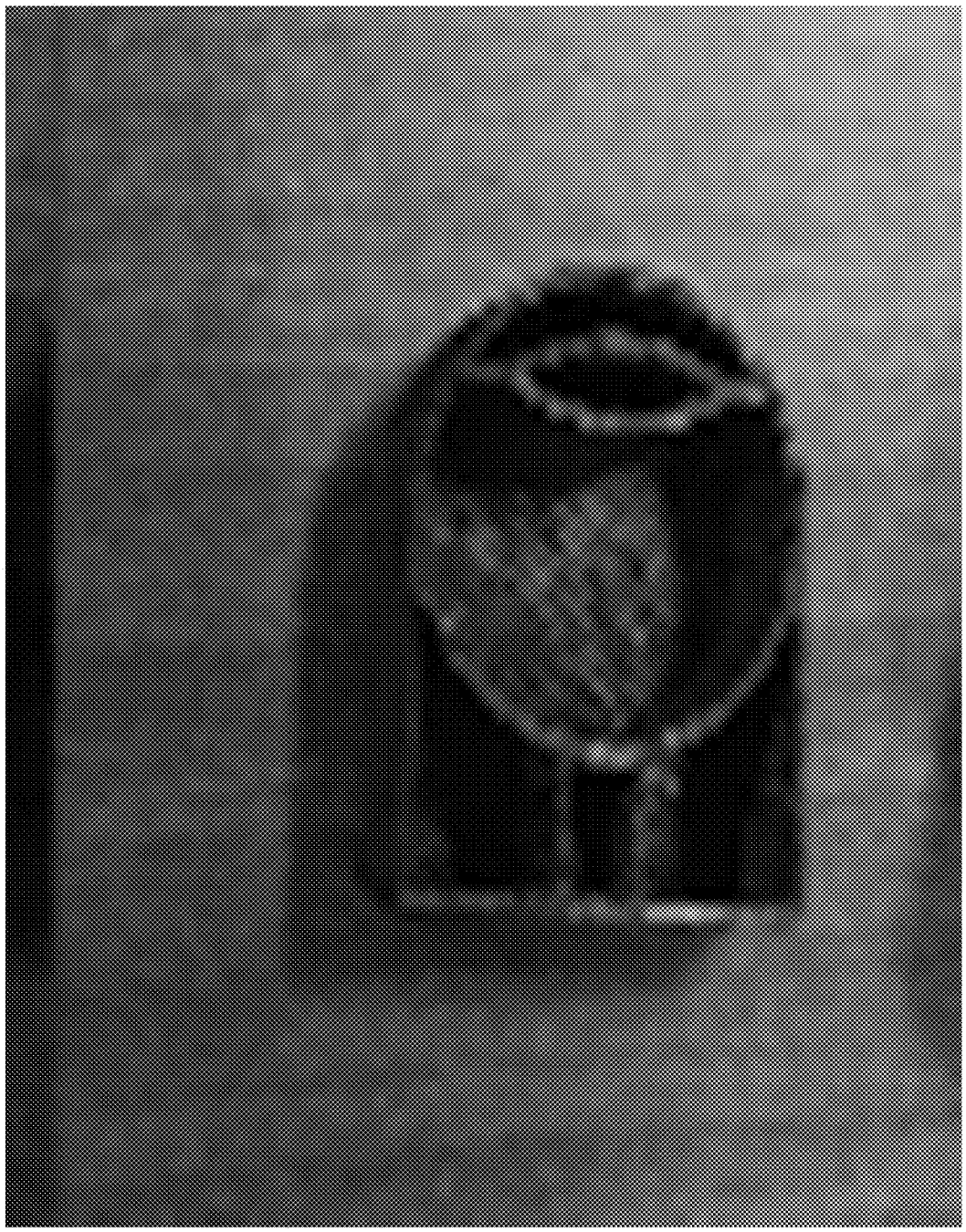
FIG. 18: Photograph of an example 3D printed model printed from ABS using a slightly thicker layer height.

A model was 3D printed out of ABS with an FDM printer using a layer height of 0.22 mm, a shell of 0.5 mm, a fill of 100% in order to eliminate possible airspace between the shell walls, a speed of 50 mm/s, a nozzle temperature of 250° C., and a bed temperature of 130° C. The printed model is pictured in FIG. 18. The model had a 1 mm wall thickness, limited by the 0.5 mm print nozzle. The ultrasound worked from the intended scan direction. It appeared that thinner walls could result in a cleaner ultrasound image.

Example 5

Figure 19:
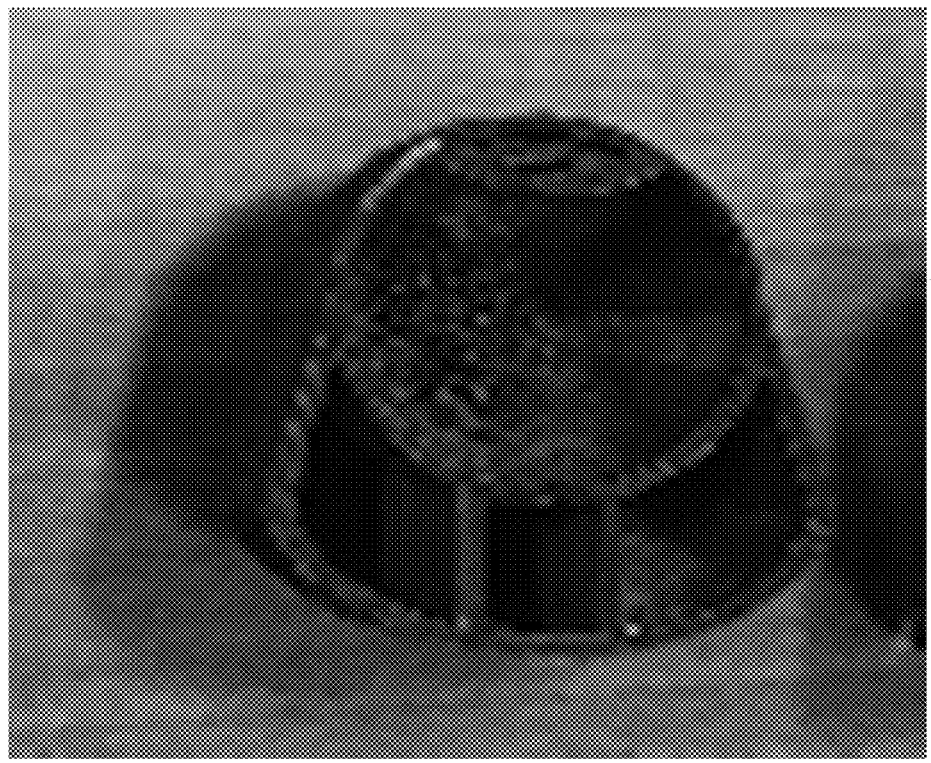
FIG. 19: Photograph of an example 3D printed model printed from ABS using a change in design of the model that included curved rear walls, a layer height of 0.22 mm, a shell of 0.5 mm, a fill of 100% in order to eliminate possible airspace between the shell walls, a speed of 50 mm/s, a nozzle temperature of 250° C., and a bed temperature of 130° C.

A model was 3D printed out of ABS with an FDM printer using a layer height of 0.15 mm in an attempt to eliminate minute air spaces between layers, a shell of 0.5 mm, a fill of 100%, a speed of 35 mm/s for less bubbling, a nozzle temperature of 240° C., and a bed temperature of 125° C. The printed model is pictured in FIG. 19. The changed print settings resulted in more clarity of the ultrasound scan. Tests were run on each setting to determine that print speed and temperature both have a noticeable impact on clarity of the scan, but layer height does not. Without wishing to be bound by theory, it is believed that this is due to lessened bubble formation during plastic extrusion. The design of the model included changes which scanned well for the eyeball itself, but it was observed that the curved wall at the rear of the model caused scan reflection artifacts.

Example 6

Figure 20:
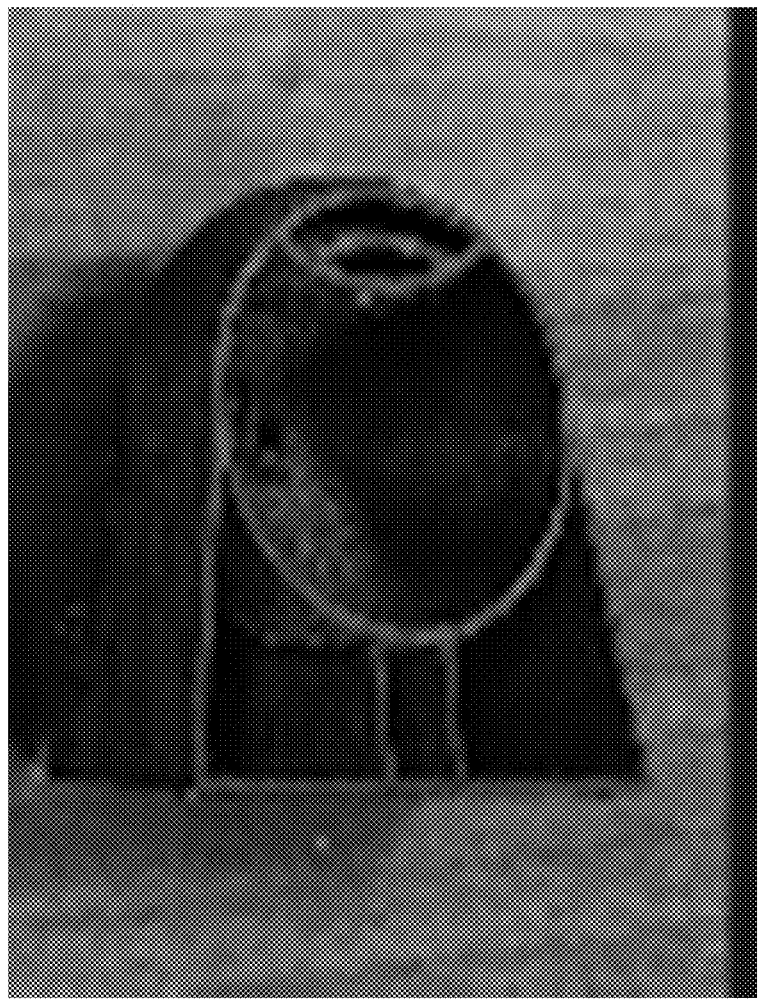
FIG. 20: Photograph of an example 3D printed model printed from ABS using straight (instead of curved) rear walls, a layer height of 0.15 mm in an attempt to eliminate minute air spaces between layers, a shell of 0.5 mm, a fill of 100%, a speed of 35 mm/s for less bubbling, a nozzle temperature of 240° C., and a bed temperature of 125° C.
Figure 21A:
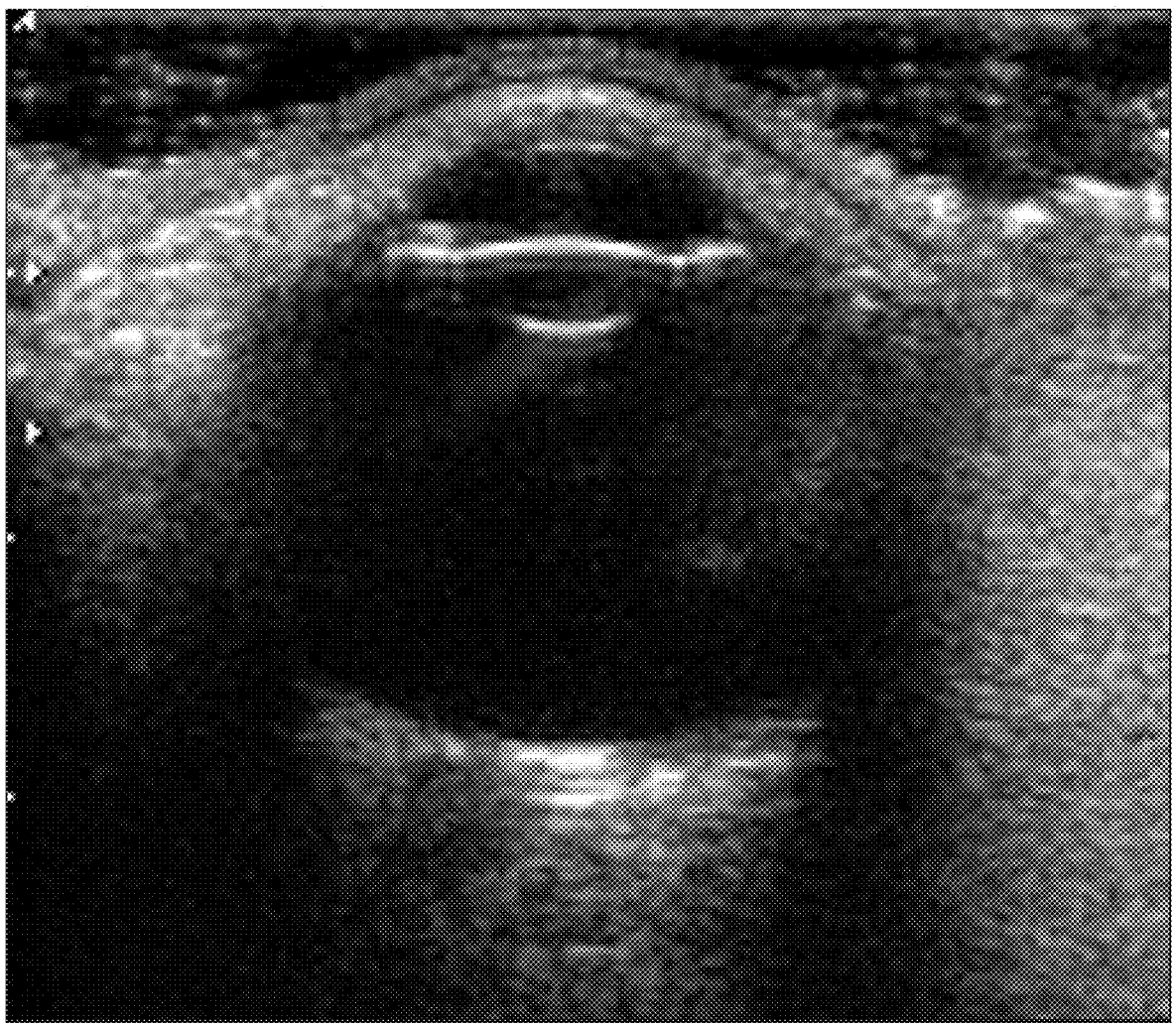
FIGS. 21A-21B: Ultrasound images of a real human eye (FIG. 21A) and an ocular ultrasound model of a normal eye (FIG. 21B).
Figure 21B:
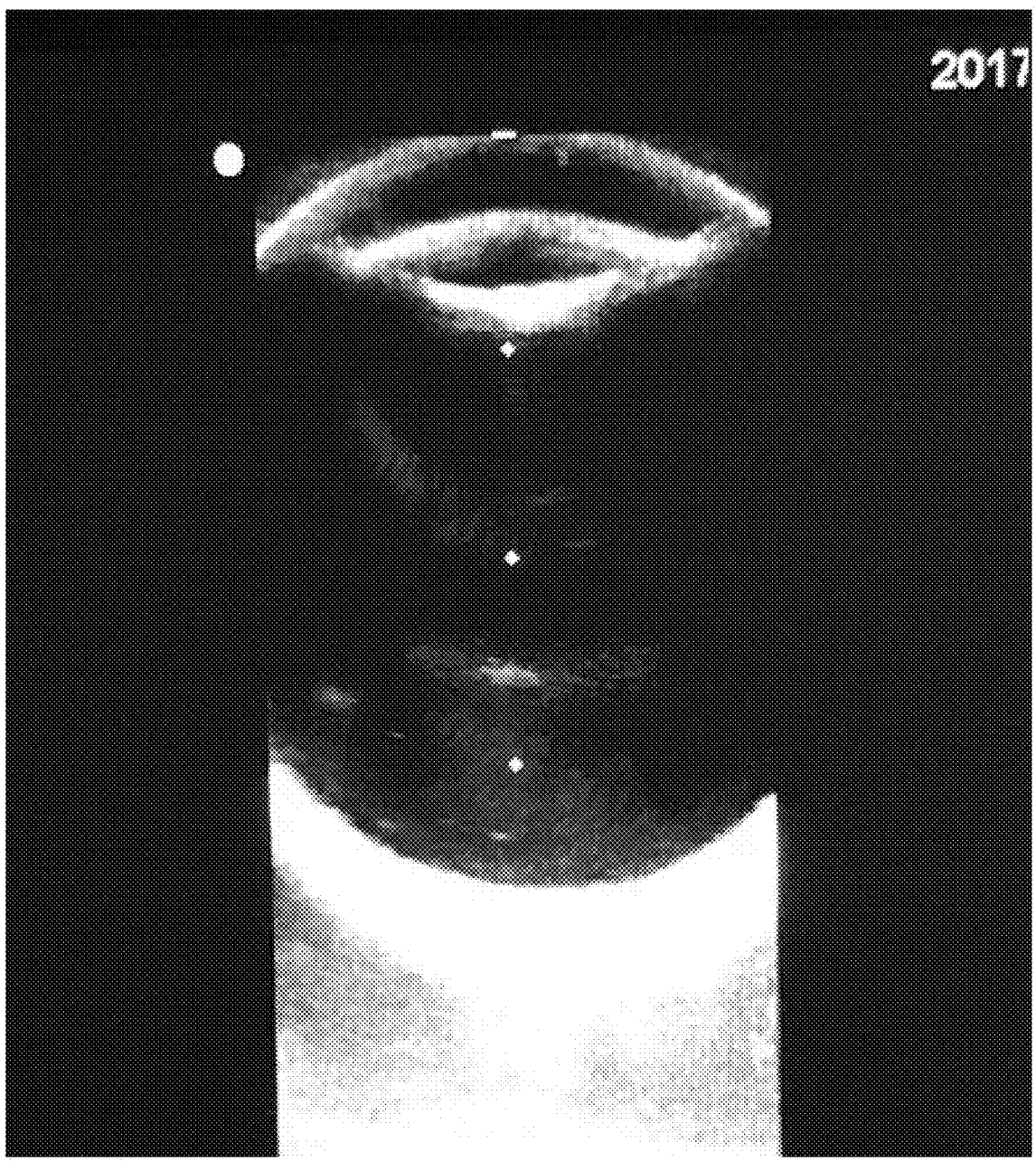

A model was 3D printed out of ABS with an FDM printer using a layer height of 0.2 mm, a shell of 0.5 mm, a fill of 100%, a speed of 35 mm/s, a nozzle temperature of 240° C., and a bed temperature of 125° C. The printed model is pictured in FIG. 20. This printed model performed well with the ultrasound scan, creating a fair representation of a human eye. Reflections on the rear wall were eliminated by making the rear walls straight instead of curved. FIG. 21A shows, for comparison, an ultrasound image of a real human eye. FIG. 21B shows an ultrasound image of the ocular ultrasound model 3D printed in this example.

Certain embodiments of the materials and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. An ocular ultrasound model comprising:
    a globe having an anterior section and a posterior section;
    a first inner wall and a second inner wall extending from the globe at the posterior section;
    a first side wall extending at a first angle from a line tangent to a middle point on a first hemisphere of the globe;
    a second side wall extending at a second angle from a line tangent to a middle point on a second hemisphere of the globe;
    a bottom wall extending between the two side walls, wherein the first and second inner walls extend from the globe to the bottom wall;
    a first ultrasoundable chamber between the first inner wall and the first side wall;
    a second ultrasoundable chamber between the second inner wall and the second side wall; and
    an optic nerve chamber between the first inner wall and the second inner wall;
    wherein the first ultrasoundable chamber and the second ultrasoundable chamber are filled with a gelatinous substance.

2. The ocular ultrasound model of claim 1, further comprising an enclosed chamber disposed within the anterior section.

3. The ocular ultrasound model of claim 2, wherein the enclosed chamber is formed from a first arc member and a second arc member, wherein the first arc member is concave and the second arc member is convex, the first arc member having a different length than the second arc member.

4. The ocular ultrasound model of claim 1, wherein the ocular ultrasound model is translucent.

5. The ocular ultrasound model of claim 1, wherein the ocular ultrasound model is flexible.

6. The ocular ultrasound model of claim 1, wherein the first and second inner walls are substantially parallel to each other.

7. The ocular ultrasound model of claim 1, comprising a plastic material, wherein the globe, the first and second inner walls, the first and second side walls, and the bottom wall all comprise the plastic material.

8. The ocular ultrasound model of claim 1, further comprising the gelatinous substance in the globe.

9. The ocular ultrasound model of claim 1, wherein the first angle approximately equals the second angle.

10. The ocular ultrasound model of claim 1, further comprising a retinal wall extending from a first point on an inner surface of the globe to a space within the globe near a second point on the inner surface, wherein the retinal wall does not cross more than half a width of the globe, the ocular ultrasound model providing a representation under ultrasound of a human eye having a retinal detachment.

11. The ocular ultrasound model of claim 1, the first and second inner walls defining the optic nerve chamber between the globe and the bottom wall, wherein the optic nerve chamber has a narrower section and a wider section, the ocular ultrasound model providing a representation under ultrasound of a human eye having increased optic nerve diameter.

12. The ocular ultrasound model of claim 1, further comprising a foreign body wall extending from an inner surface of the globe, the ocular ultrasound model providing a representation under ultrasound of a human eye having an intraocular foreign body.

13. The ocular ultrasound of model of claim 1, further comprising a speckled area within the globe defined by a curvy wall extending between two points on an inner surface of the globe, wherein the curvy wall crosses over more than half a width of the globe, the ocular ultrasound model providing a representation under ultrasound of a human eye having a vitreous hemorrhage.

14. The ocular ultrasound model of claim 1, further comprising a speckled area defined by a curvy wall extending from a first point on an inner surface of the globe to a space near, but not touching, a second point on the inner surface, wherein the curvy wall crosses over more than half a width of the globe, the ocular ultrasound model providing a representation under ultrasound of a human eye having a vitreous detachment.

15. The ocular ultrasound model of claim 1, further comprising a dislocated lens chamber formed in the posterior section of the globe, the ocular ultrasound model providing a representation under ultrasound of a human eye having a dislocated lens.

16. The ocular ultrasound model of claim 15, further comprising a curvy wall extending from a first point on an inner surface of the globe to a second point on the inner surface of the globe, wherein the curvy wall defines a reduced globe space between the first arc and the curvy wall having a volume less than the volume of a space between the curvy wall and the globe in the posterior section, the ocular ultrasound model providing a representation under ultrasound of a human eye having a ruptured globe.

17. The ocular ultrasound model of claim 1, further comprising a foreign body wall extending from an inner surface of the globe, and a speckled area within the globe defined by a curvy wall extending between two points on an inner surface of the globe, wherein the curvy wall crosses over more than half a width of the globe, the ocular ultrasound model providing a representation under ultrasound of a human eye having an intraocular foreign body and a vitreous hemorrhage.

18. An ocular ultrasound training simulator comprising:
a representation of a human head having two sockets each configured to receive an ocular ultrasound model; and
an ocular ultrasound model of claim 1 configured to be inserted in at least one of the sockets.

19. An ocular ultrasound model comprising:
a globe having an anterior section and a posterior section, wherein the globe has an inner surface and an outer surface;
either first and second inner walls extending from the globe at the posterior section;
a first arc member within the globe extending between two points on the inner surface, wherein the first arc member comprises an anterior surface and a posterior surface;
a second arc member within the globe extending between two points on the anterior surface of the first arc member;
a first ultrasoundable chamber adjacent to the first inner wall;
a second ultrasoundable chamber adjacent to the second inner wall; and
an optic nerve chamber between the first inner wall and the second inner wall;
wherein the first ultrasoundable chamber and the second ultrasoundable chamber are filled with a gelatinous substance; and
wherein the first arc member and the second arc member define two chambers within the anterior section of the globe.

20. The ocular ultrasound model of claim 19, wherein one of the first arc member or the second arc member is concentric with the globe.

21. The ocular ultrasound model of claim 19, wherein the ocular ultrasound model is filled with the gelatinous substance.

22. An ocular ultrasound model comprising:
a substantially spherical globe comprising a first enclosed chamber which provides a representation, upon application of ultrasound waves, of a lens of a human eye, wherein the first enclosed chamber is filled with a gelatinous substance;
a first side wall, a second side wall, a first inner wall, and a second inner wall extending from the globe;
a first ultrasoundable chamber between the first inner wall and the first side wall;
a second ultrasoundable chamber between the second inner wall and the second side wall; and
an optic nerve chamber between the first inner wall and the second inner wall, wherein the optic nerve chamber provides a representation, upon application of ultrasound waves, of an optic nerve of a human eye;
wherein the globe, the first enclosed chamber, the first inner wall, the second inner wall, the first side wall, and the second side wall are formed from a plastic material.

23. The ocular ultrasound model of claim 22, wherein the plastic material comprises acrylonitrile butadiene styrene (ABS) or polylactic acid (PLA).

24. The ocular ultrasound model of claim 22, wherein the globe further comprises a second enclosed chamber filled with the gelatinous substance, wherein the second enclosed chamber provides a representation, upon application of ultrasound waves, of a vitreous body of a human eye.

* * * * *